(12) United States Patent
Barth et al.

(10) Patent No.: US 8,383,666 B2
(45) Date of Patent: Feb. 26, 2013

(54) PYRROLE DERIVATIVES, PREPARATION OF SAME AND THERAPEUTIC APPLICATION THEREOF

(75) Inventors: Francis Barth, Paris (FR); Audrey Jeanjean, Paris (FR); Murielle Rinaldi-Carmona, Paris (FR); Christian Congy, Paris (FR)

(73) Assignee: Sanofi, Paris (FR)

( * ) Notice: Subject to any disclaimer, the term of this patent is extended or adjusted under 35 U.S.C. 154(b) by 86 days.

(21) Appl. No.: 12/942,784

(22) Filed: Nov. 9, 2010

(65) Prior Publication Data
US 2011/0144157 A1 Jun. 16, 2011

Related U.S. Application Data

(63) Continuation of application No. PCT/FR2009/000536, filed on May 7, 2009.

(30) Foreign Application Priority Data

May 9, 2008 (FR) .................................... 08 02553

(51) Int. Cl.
 A61K 31/4025 (2006.01)
 A61K 31/445 (2006.01)
 C07D 207/30 (2006.01)
 C07D 401/02 (2006.01)
(52) U.S. Cl. ........ 514/423; 548/530; 548/537; 546/184; 546/208; 514/315; 514/317
(58) Field of Classification Search ............... 548/530, 548/537; 546/184, 192, 208; 514/315, 317, 514/423
See application file for complete search history.

(56) References Cited

U.S. PATENT DOCUMENTS

| 7,381,727 B2 * | 6/2008 | Barth et al. ............... 514/254.01 |
| 7,879,902 B2 * | 2/2011 | Barth et al. ................... 514/423 |
| 8,044,072 B2 * | 10/2011 | Barth et al. ................... 514/326 |

FOREIGN PATENT DOCUMENTS

| FR | 0408773 | 8/2004 |
| FR | 0610202 | 11/2006 |

OTHER PUBLICATIONS

Bouaboula, et al., A Selective Inverse Agonist for Central Cannabinoid Receptor Inhibits Mitogen-Activated Protein Kinase Activation Stimulated by Insulin or Insulin-Like Growth Factor 1, The Journal of Biological Chemistry, vol. 272, No. 35, (1997), pp. 22330-22339.
Bouaboula, et al., Stimulation of Cannabinoid Receptor CB1 induces Krox-24 Expression in Human Astrocytoma Cells, The Journal of Biological Chemistry, vol. 270, No. 23, (1995), pp. 13973-13980.
Feldman, et al., A Novel Route to the 4-Anilido-4-(Methoxycarbonyl)Piperidine Class of Analgetics, J. Org. Chem., vol. 55, (1990), pp. 4207-4209.
Rinaldi-Carmona et al., SR147778 [5-(4-Bromophenyl)-1-(2,4-Dichlorophenyl)-4-ethyl-N-(1-Piperidinyl)-1H-Pyrazole-3-Carboxamide], A New Potent and Selective Antagonist of the CB1 Cannabinoid Receptor: Biochemical and Pharmacological Characterization, The Journal of Pharmacology and Experimental Therapeutics, 2004 (310)3 pp. 905-914.
Rinaldi-Carmona, et al., SR141716A, A Potent and Selective Antagonist of the Brain Cannabinoid Receptor, FEBS Letters, (1994), pp. 240-244, vol. 350.
Rinaldi-Carmona, et al., Biochemical and Pharmacological Characterisation of SR141716A, The First Potent and Selective Brain Cannabinoid Receptor Antagonist, Life Sciences, vol. 56, No. 23/24, pp.1941-1947, (1995).
Rinaldi-Carmona, et al., Characterization of Two Cloned Human CB1 Cannabinoid Receptor Isoforms, The Journal of Pharmacology and Experimental Therapeutics, vol. 275, No. 2, pp. 871-876, (1996).
Westeringh, et al., 4-Substituted Piperidines. I, Derivatives of 4-T-Amino-4-Piperidinecarboxamides, Journal of Medicinal Chemistry, (1964), vol. 7, No. 5, 619-623.
Knight, et al., An Approach to 2,3-Dihydropyrroles and B-Iodopyrroles Based on 5-Endo-Dig Cyclisations, J. Chem. Soc., Perkin Trans., vol. 1, pp. 622-628, (2002).
International Search Report for W02009/141533 dated Nov. 26, 2009.

* cited by examiner

*Primary Examiner* — Golam M M Shameem
(74) *Attorney, Agent, or Firm* — Scully, Scott, Murphy & Presser, P.C.

(57) ABSTRACT

The subject of the invention is Compound of Formula (I):

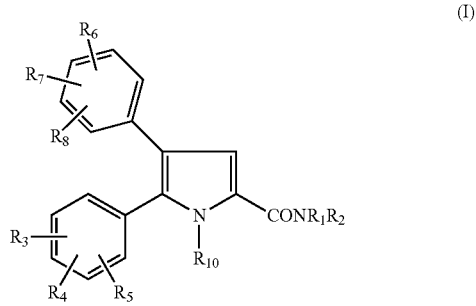

in which R1-R8 and R10 are defined within, its method of preparation, and its therapeutic application.

10 Claims, No Drawings

PYRROLE DERIVATIVES, PREPARATION OF SAME AND THERAPEUTIC APPLICATION THEREOF

The present invention relates to 4,5-diarylpyrrole-2-carboxamide derivatives, to the preparation thereof and to the therapeutic use thereof.

4,5-diphenylpyrrole-2-carboxamide derivatives having an affinity for cannabinoid $CB_1$ receptors have been described in Patent Application WO 2006/024 777. Novel 4,5-diarylpyrrole-2-carboxamide derivatives bearing a particular substituent on one of the aryl groups, which have cannabinoid $CB_1$ receptor antagonist properties, have now been found. In particular, these novel derivatives have peripheral CB1 receptor antagonist properties and exhibit weak penetration into the brain.

The subject of the present invention is compounds corresponding to the formula:

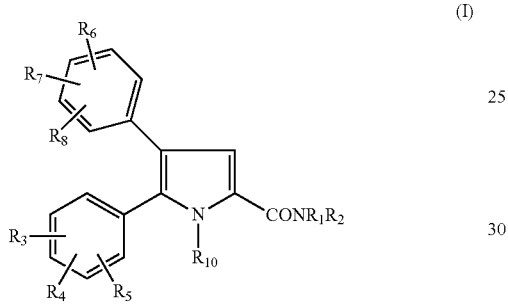

(I)

in which:
$R_1$ represents a hydrogen atom or a $(C_1-C_4)$alkyl group which is unsubstituted or substituted with one or more fluorine atoms;
$R_2$ represents:
either a homopiperidin-1-yl, piperidin-1-yl, pyrrolidin-1-yl or azetidin-1-yl radical, said radicals being unsubstituted or substituted once or twice with a substituent, each chosen independently from a fluorine atom, a $(C_1-C_4)$alkyl, $(C_1-C_4)$alkoxy, trifluoromethyl, —$OCF_3$, —$CH_2OH$ or —$CONH_2$ and/or a phenyl group, said phenyl group being unsubstituted or substituted once or twice with a substituent, each chosen independently from a halogen atom, a —$CF_3$ group, a methoxy group and/or a trifluoromethoxy group;
or an amino$(C_1-C_6)$alkyl group which is unsubstituted or substituted with one or more substituents, each chosen independently from a fluorine atom, a hydroxyl group, a —$CONH_2$ group and/or a phenyl group, said phenyl group being unsubstituted or substituted once or twice with a substituent, each chosen independently from a halogen atom, a —$CF_3$ group, a methoxy group and/or a trifluoromethoxy group;
or $R_1$ and $R_2$, together with the nitrogen atom to which they are attached, constitute:
either a piperazin-1-yl or 1,4-diazepan-1-yl radical, said radicals being unsubstituted or substituted with a substituent chosen from a phenyl, benzodioxolyl, benzodioxolylmethyl, tetrahydrofuranylcarbonyl, —$COR_{11}$, and/or —$CH_2COR_{11}$ group, the phenyl group itself being unsubstituted or substituted one or more times with a substituent, each chosen independently from a halogen atom, or a $(C_1-C_4)$alkyl, trifluoromethyl, hydroxyl, $(C_1-C_4)$alkoxy and/or cyano group;
or a homopiperidin-1-yl, piperidin-1-yl, pyrrolidin-1-yl or azetidin-1-yl radical, said radicals being unsubstituted or substituted once or twice with a substituent, each independently chosen from:
a fluorine atom, or a cyano, —$COR_{11}$, —$NR_{12}R_{13}$, —$NHCOR_{14}$, —$CH_2COR_{11}$, —$SO_2R_{14}$, and/or —$SO_2NR_{12}R_{13}$ group;
and/or a phenyl group or a pyridinyl group; said groups being unsubstituted or substituted one or more times with a substituent, each chosen independently from a halogen atom, or a $(C_1-C_4)$alkyl, trifluoromethyl, hydroxyl, $(C_1-C_4)$alkoxy and/or cyano group;
and/or a benzyl group which is unsubstituted or substituted one or more times with a substituent, each chosen independently from a halogen atom, or a $(C_1-C_4)$alkyl, trifluoromethyl, hydroxyl, $(C_1-C_4)$alkoxy and/or cyano group;
and/or a piperidin-1-yl, pyrrolidin-1-yl or azetidin-1-yl group, said groups being unsubstituted or substituted one or more times with a substituent, each chosen independently from a fluorine atom, or a $(C_1-C_4)$alkyl, $(C_1-C_4)$alkoxy, hydroxyl, trifluoromethyl and/or $OCF_3$ group;
and/or an aminophenyl or aminobenzyl group, said groups being unsubstituted or substituted one or more times with a substituent, each chosen independently from a halogen atom, or a $(C_1-C_4)$alkyl, trifluoromethyl, hydroxyl, $(C_1-C_4)$alkoxy and/or cyano group;
and/or an amino$(C_1-C_6)$alkyl group which is unsubstituted or substituted one or more times with a substituent, each chosen independently from a halogen atom, a hydroxyl group, a $(C_1-C_4)$alkoxy group and/or a cyano group;
and/or an amino$(C_3-C_7)$cycloalkyl group which is unsubstituted or substituted one or more times with a substituent, each chosen independently from a halogen atom, a hydroxyl group, a $(C_1-C_4)$alkyl group, a $(C_1-C_4)$alkoxy group and/or a cyano group, said $(C_1-C_4)$alkyl group being unsubstituted or substituted one or more times with a fluorine atom;
$R_3$, $R_4$, $R_5$, $R_6$, $R_7$, $R_8$ each independently represent a hydrogen atom, a halogen atom, a —ON, —$S(O)_nR_{14}$ or —$OSO_2R_{14}$ group, or a $(C_1-C_6)$alkyl group which is unsubstituted or substituted one or more times with a fluorine atom and/or a $(C_1-C_6)$alkoxy group which is unsubstituted or substituted with one or more fluorine atoms, on the condition that one of the two substituents $R_3$ and $R_6$ represents a Y-A-$R_9$ group;
Y represents a direct bond, an oxygen atom, or an —$S(O)_n$—, —$OSO_2$— or —$N(R_{18})$— group;
A represents a $(C_1-C_4)$ alkylene group which is unsubstituted or substituted one or more times with a substituent, each chosen independently from a $(C_1-C_3)$alkyl group and/or with a fluorine atom;
$R_9$ represents an —$OR_{12}$, —CN, —$CO_2H$, $NR_{12}R_{13}$, —$CONR_{12}R_{13}$, —$NR_{15}COR_{12}$, —$CONHNH_2$, —CONHOH, —$CONHSO_2R_{14}$, —$S(O)_nR_{14}$, —$SO_2NR_{12}R_{13}$, —$NR_{18}SO_2R_{14}$ or —$NR_{15}SO_2NR_{12}R_{13}$, or an aromatic heterocycle chosen from:

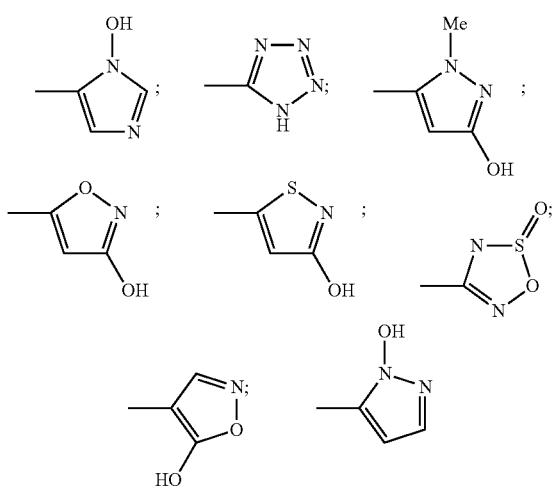

$R_{10}$ represents a hydrogen or a $(C_1-C_4)$alkyl group;
$R_{11}$ represents:
  a $(C_1-C_4)$alkyl, phenyl, benzyl, $(C_1-C_4)$alkoxy or $(C_1-C_3)$alkylene-O—$(C_1-C_3)$alkyl group, said groups being unsubstituted or substituted with one or more substituents, each chosen independently from a $(C_1-C_4)$alkoxy group, a hydroxyl group and/or a fluorine atom;
  a trifluoromethyl;
  and/or an —$NR_{16}R_{17}$ group;
$R_{12}$ and $R_{13}$ each independently represent a hydrogen atom or a $(C_1-C_6)$alkyl group optionally substituted with one or more substituents, each chosen independently from a fluorine atom, —OH and/or —$OR_{14}$,
or $R_{12}$ and $R_{13}$, together with the nitrogen atom to which they are attached, constitute a 4- to 7-membered heterocyclic radical which may comprise a second heteroatom chosen from a nitrogen, oxygen or sulphur atom;
n represents 0, 1 or 2;
$R_{14}$ represents a $(C_1-C_4)$alkyl group which is unsubstituted or substituted with one or more fluorine atoms;
$R_{15}$ represents a hydrogen atom or a $(C_1-C_4)$alkyl group;
$R_{16}$ and $R_{17}$ each independently represent:
  a hydrogen atom;
  and/or a benzyl group which is unsubstituted or substituted one or more times with a substituent, each chosen independently from a halogen atom, or a $(C_1-C_4)$alkyl, trifluoromethyl, hydroxyl, $(C_1-C_4)$alkoxy and/or cyano group;
  and/or a $(C_1-C_6)$alkyl group optionally substituted with one or more substituents, each chosen independently from a halogen atom, —OH and/or —$OR_{14}$;
$R_{18}$ represents a hydrogen atom or a $(C_1-C_4)$alkyl group which is unsubstituted or substituted with one or more fluorine atoms;
in the form of bases (=correspond to the free forms of the compounds) and also the pharmaceutically acceptable salts thereof or the salts thereof that are acceptable for the purification and/or isolation of said compounds of Formula (I).

The compounds of Formula (I) may comprise one or more asymmetrical carbon atoms. They may therefore exist in the form of enantiomers or of diastereoisomers. These enantiomers and diastereoisomers, and also mixtures thereof, including racemic mixtures, are part of the invention.

The compounds of Formula (I) may exist in the form of bases (i.e. such as in the free forms thereof), of addition salts with acids or of addition salts with bases. These salts are advantageously prepared with pharmaceutically acceptable salts, but the salts of other acids that are useful, for example, for purifying or isolating the compounds of Formula (I) are also part of the invention.

The term "$(C_1-C_3)$alkyl group", "$(C_1-C_4)$alkyl group" or "$(C_1-C_6)$alkyl group" is intended to mean, respectively, a linear or branched alkyl radical containing from one to three carbon atoms, from one to four carbon atoms or from one to six carbon atoms, such as the methyl, ethyl, propyl, isopropyl, butyl, isobutyl, sec-butyl, tert-butyl, pentyl, isopentyl, n-hexyl or isohexyl radical. Methyl and ethyl groups are preferred for a $(C_1-C_3)$alkyl, for a $(C_1-C_4)$alkyl and for a $(C_1-C_6)$alkyl. More particularly, the methyl group is preferred.

The "alkylene group" is intended to mean a linear divalent carbon-based radical, such as —($CH_2$)—, —($CH_2$)$_2$—, —($CH_2$)$_3$—, —($CH_2$)$_4$— or —($CH_2$)$_5$—.

The term "$(C_1-C_4)$alkoxy" is intended to mean an oxygen atom bonded to a linear or branched carbon-based radical containing from one to four carbon atoms, such as the methoxy, ethoxy, propoxy, isopropoxy, butoxy, sec-butoxy or tert-butoxy radical. The methoxy group is preferred.

The term "halogen atom" is intended to mean a fluorine, chlorine, bromine or iodine atom; fluorine, chlorine or bromine atoms being preferred.

The term "aminocycloalkyl group" is intended to mean, for the cycloalkyl part, a cyclopropyl, cyclobutyl, cyclopentyl, cyclohexyl or cycloheptyl carbon-based radical.

The expression "saturated or unsaturated, 4- to 7-membered heterocyclic radical which may or may not contain a second heteroatom, such as O, N or S" is intended to mean in particular radicals such as homopiperidin-1-yl morpholin-4-yl, piperidin-1-yl, piperazin-1-yl, pyrrolidin-1-yl or azetidin-1-yl, piperidin-1-yl and pyrrolidin-1-yl radicals being preferred.

According to the present invention, the following stand out:
  the compounds of Formula (IA) in which Y represents an oxygen atom;
  the compounds of Formula (IB) in which Y corresponds to a direct bond;
  the compounds of Formula (IC) in which Y represents an —S(O)$_n$— group;
  the compounds of Formula (ID) in which Y represents an —O(SO$_2$)— group;
  and the compounds of Formula (IE) in which Y represents an —N($R_{18}$)— group;
  the other substituents being as defined for the compounds of Formula (I).

Within the compounds of Formulae (I), (IA), (IB), (IC), (ID) and (IE), the following in particular stand out:
  the compounds in which the substituent $R_6$ represents a Y-A-$R_9$ group and the substituent $R_3$ represents a hydrogen atom, a halogen atom, a —CN, —S(O)$_n R_{14}$ or —OSO$_2 R_{14}$ group, a $(C_1-C_6)$alkyl group which is unsubstituted or substituted one or more times with a fluorine atom, or a $(C_1-C_6)$alkoxy group which is unsubstituted or substituted with one or more fluorine atoms;
  and the compounds in which the substituent $R_3$ represents a Y-A-$R_9$ group and the substituent $R_6$ represents a hydrogen atom, a halogen atom, a —CN, —S(O)$_n R_{14}$ or —OSO$_2 R_{14}$ group, a $(C_1-C_6)$alkyl group which is unsubstituted or substituted one or more times with a fluorine atom, or a $(C_1-C_6)$alkoxy group which is unsubstituted or substituted with one or more fluorine atoms;

the other substituents being as defined above for the compounds of Formula (I).

According to the present invention, preference is given to the compounds of Formula (I) in which:

A represents an unsubstituted ($C_1$-$C_4$) alkylene group;
$R_9$ represents an —$OR_{12}$, —$NR_{12}R_{13}$, —$CONR_{12}R_{13}$, —$NR_{15}COR_{12}$, —$CONHNH_2$, —$CONHOH$, —$S(O)_nR_{14}$, —$SO_2NR_{12}R_{13}$, —$NR_{18}SO_2R_{14}$ or —$NR_{15}SO_2NR_{12}R_{13}$ group;
and the other substituents being as defined above for the compounds of Formula (I).

In particular, for Y, an oxygen atom is preferred.

In particular, for $R_9$, an —$OR_{12}$, —$NR_{12}R_{13}$, —$CONR_{12}R_{13}$, —$NR_{15}COR_{12}$ or —$NR_{18}SO_2R_{14}$ group is preferred.

According to a first variant, preference is given to the compounds of Formulae (IA), (IB), (IC), (ID) and/or (IE) in which:

$R_1$ represents a hydrogen atom or a ($C_1$-$C_4$)alkyl group which is unsubstituted or substituted with one or more fluorine atoms;

$R_2$ represents:
either a homopiperidin-1-yl, piperidin-1-yl, pyrrolidin-1-yl or azetidin-1-yl radical, said radicals being substituted once or twice with a substituent, each chosen independently from a fluorine atom, a ($C_1$-$C_4$)alkyl, ($C_1$-$C_4$)alkoxy, trifluoromethyl, —$OCF_3$, —$CH_2OH$ or —$CONH_2$ group and/or a phenyl group, said phenyl group being unsubstituted or substituted once or twice with a substituent, each chosen independently from a halogen atom, a —$CF_3$ group, a methoxy group and/or a trifluoromethoxy group;

or an amino($C_1$-$C_6$)alkyl group substituted with one or more substituents, each chosen independently from a fluorine atom, a hydroxyl group, a —$CONH_2$ group and/or a phenyl group, said phenyl group being unsubstituted or substituted once or twice with a substituent, each independently chosen from a halogen atom, a —$CF_3$ group, a methoxy group and/or a trifluoromethoxy group;

the other substituents being as defined for the compounds of Formula (I).

For this first variant, preference is given to the compounds in which the $R_2$ radical represents in particular a homopiperidin-1-yl, piperidin-1-yl, pyrrolidin-1-yl or azetidin-1-yl radical, said radicals being substituted once or twice with a substituent, each chosen independently from a fluorine atom, a ($C_1$-$C_4$)alkyl, ($C_1$-$C_4$)alkoxy, trifluoromethyl, —$OCF_3$, —$CH_2OH$ or —$CONH_2$ group and/or a phenyl group, said phenyl group being unsubstituted or substituted once or twice with a substituent, each chosen independently from a halogen atom, a —$CF_3$ group, a methoxy group and/or a trifluoromethoxy group.

For this first variant, preference is given to the compounds in which $R_1$ represents in particular a hydrogen atom.

According to a second variant, preference is given to the compounds of Formulae (IA), (IB), (IC), (ID) and/or (IE) in which:

$R_1$ and $R_2$, together with the nitrogen atom to which they are linked, constitute:
either a piperazin-1-yl or 1,4-diazepan-1-yl radical, said radicals being substituted with a substituent chosen from a phenyl, benzodioxolyl, benzodioxolylmethyl, tetrahydrofuranylcarbonyl, —$COR_{11}$ and/or —$CH_2COR_{11}$ group, the phenyl group itself being unsubstituted or substituted one or more times with a substituent, each chosen independently from a halogen atom, a ($C_1$-$C_4$)alkyl group, a trifluoromethyl group, a hydroxyl group, a ($C_1$-$C_4$)alkoxy group and/or a cyano group;

or a homopiperidin-1-yl, piperidin-1-yl, pyrrolidin-1-yl or azetidin-1-yl radical, said radicals being substituted once or twice with a substituent, each chosen independently from:
a fluorine atom, or a cyano, —$COR_{11}$, —$NR_{12}R_{13}$, —$NHCOR_{14}$, —$CH_2COR_{11}$, —$SO_2R_{14}$ and/or —$SO_2NR_{12}R_{13}$ group;
and/or a phenyl or pyridinyl group; said groups being unsubstituted or substituted one or more times with a substituent, each chosen independently from a halogen atom, a ($C_1$-$C_4$)alkyl group, a trifluoromethyl group, a hydroxyl group, a ($C_1$-$C_4$)alkoxy group and/or a cyano group;
and/or a benzyl group substituted one or more times with a substituent, each chosen independently from a halogen atom, a ($C_1$-$C_4$)alkyl group, a trifluoromethyl group, a hydroxyl group, a ($C_1$-$C_4$)alkoxy group and/or a cyano group;
and/or a piperidin-1-yl, pyrrolidin-1-yl or azetidin-1-yl group, said groups being unsubstituted or substituted one or more times with a substituent, each chosen independently from a fluorine atom, a ($C_1$-$C_4$)alkyl group, a ($C_1$-$C_4$)alkoxy group, a hydroxyl group, a trifluoromethyl group and/or an —$OCF_3$ group;
and/or an aminophenyl or aminobenzyl group, said groups being unsubstituted or substituted one or more times with a substituent, each chosen independently from a halogen atom, a ($C_1$-$C_4$)alkyl group, a trifluoromethyl group, a hydroxyl group, a ($C_1$-$C_4$)alkoxy group and/or a cyano group;
and/or an amino ($C_1$-$C_6$)alkyl group which is unsubstituted or substituted one or more times with a substituent, each chosen independently from a halogen atom, a hydroxyl group, a ($C_1$-$C_4$)alkoxy group and/or a cyano group;
and/or an amino ($C_3$-$C_7$)cycloalkyl group which is unsubstituted or substituted one or more times with a substituent, each chosen independently from a halogen atom, a hydroxyl group, a ($C_1$-$C_4$)alkyl group, a ($C_1$-$C_4$)alkoxy group and/or a cyano group, said ($C_1$-$C_4$)alkyl group being unsubstituted or substituted one or more times with a fluorine atom;

the other substituents being as defined for the compounds of Formula (I).

In particular, for this second variant, preference is given to the compounds in which:

$R_1$ and $R_2$, together with the nitrogen atom to which they are attached, constitute a homopiperidin-1-yl, piperidin-1-yl, pyrrolidin-1-yl or azetidin-1-yl radical, said radicals being substituted once or twice with a substituent, each chosen independently from:
a fluorine atom, or a cyano, —$COR_{11}$, —$NR_{12}R_{13}$, —$NHCOR_{14}$, —$CH_2COR_{11}$, —$SO_2R_{14}$ and/or —$SO_2NR_{12}R_{13}$ group;
and/or a phenyl or pyridinyl group; said groups being unsubstituted or substituted one or more times with a substituent, each chosen independently from a halogen atom, a ($C_1$-$C_4$)alkyl group, a trifluoromethyl group, a hydroxyl group, a ($C_1$-$C_4$)alkoxy group and/or a cyano group;
and/or a benzyl group substituted one or more times with a substituent, each chosen independently from a halogen atom, a ($C_1$-$C_4$)alkyl group, a trifluoromethyl group, a hydroxyl group, a ($C_1$-$C_4$)alkoxy group and a cyano group;

and/or a piperidin-1-yl, pyrrolidin-1-yl or azetidin-1-yl group, said groups being unsubstituted or substituted one or more times with a substituent, each chosen independently from a fluorine atom, a ($C_1$-$C_4$)alkyl group, a ($C_1$-$C_4$)alkoxy group, a hydroxyl group, a trifluoromethyl group and/or an —$OCF_3$ group;

and/or an aminophenyl or aminobenzyl group, said groups being unsubstituted or substituted one or more times with a substituent, each chosen independently from a halogen atom, a ($C_1$-$C_4$)alkyl group, a trifluoromethyl group, a hydroxyl group, a ($C_1$-$C_4$)alkoxy group and/or a cyano group;

and/or an amino($C_1$-$C_6$)alkyl group which is unsubstituted or substituted one or more times with a substituent, each chosen independently from a halogen atom, a hydroxyl group, a ($C_1$-$C_4$)alkoxy group and/or a cyano group;

and/or an amino ($C_3$-$C_7$)cycloalkyl group which is unsubstituted or substituted one or more times with a substituent, each chosen independently from a halogen atom, a hydroxyl group, a ($C_1$-$C_4$)alkyl group, a ($C_1$-$C_4$)alkoxy group and/or a cyano group, said ($C_1$-$C_4$)alkyl group being unsubstituted or substituted one or more times with a fluorine atom;

the other substituents being as defined for the compounds of Formula (I).

Among the compounds according to the invention, mention may in particular be made of the compounds hereinafter, as they are and also the salts thereof:

| IUPAC Name | Chemical Structure |
| --- | --- |
| 1'-[5-(4-(3-aminopropoxy)phenyl)-4-(2,4-dichlorophenyl)-1-methyl-1H-pyrrole-2-carbonyl]-[1,4']bipiperidinyl-4'-carboxamide | 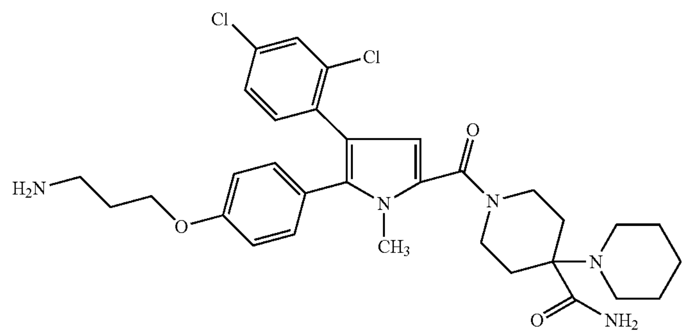 [SMILES: Cn1c(C(=O)N2CCC(C(N)=O)(N3CCCCC3)CC2)cc(-c2ccc(Cl)cc2Cl)c1-c1ccc(OCCCN)cc1] |
| 1'-[5-[4-(3-carbamoylpropoxy)-phenyl]-4-(2,4-dichlorophenyl)-1-methyl-1H-pyrrole-2-carbonyl]-[1,4']bipiperidinyl-4'-carboxamide | 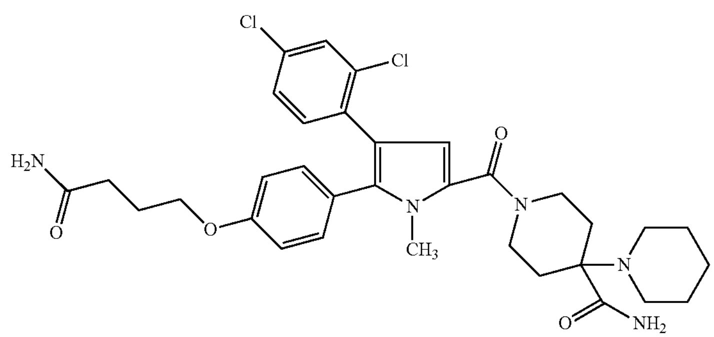 [SMILES: Cn1c(C(=O)N2CCC(C(N)=O)(N3CCCCC3)CC2)cc(-c2ccc(Cl)cc2Cl)c1-c1ccc(OCCCC(N)=O)cc1] |
| 1'-[4-(2,4-dichlorophenyl)-5-(4-(3-methanesulphonylaminopropoxy)-phenyl)-1-methyl-1H-pyrrole-2-carbonyl]-[1,4']bipiperidinyl-4'-carboxamide | 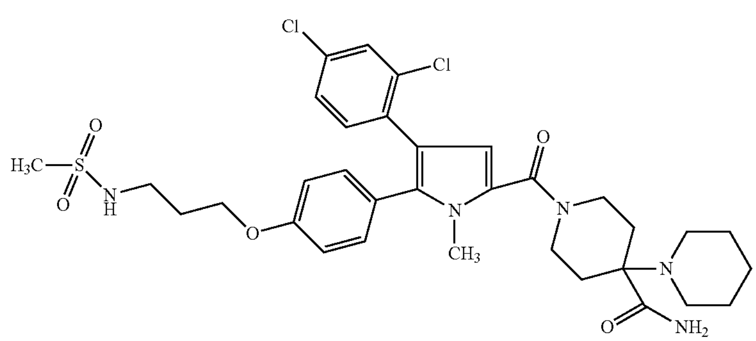 [SMILES: Cn1c(C(=O)N2CCC(C(N)=O)(N3CCCCC3)CC2)cc(-c2ccc(Cl)cc2Cl)c1-c1ccc(OCCCNS(C)(=O)=O)cc1] |

| IUPAC Name | Chemical Structure |
|---|---|
| 1'-[5-(4-carbamoylmethoxyphenyl)-4-(2,4-dichlorophenyl)-1-methyl-1H-pyrrole-2-carbonyl]-[1,4']bipiperidinyl-4'-carboxamide | 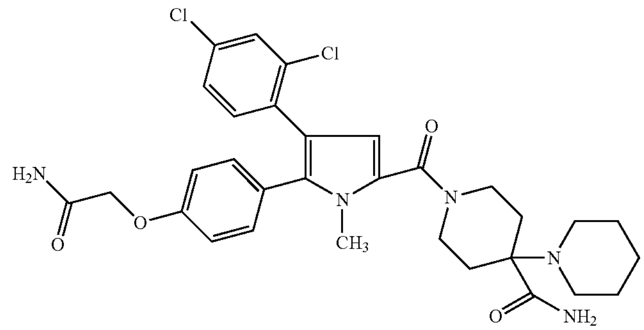 [SMILES: Cn1c(C(=O)N2CCC(C(N)=O)(N3CCCCC3)CC2)cc(-c2ccc(Cl)cc2Cl)c1-c1ccc(OCC(N)=O)cc1] |
| 1'-(4-(2,4-dichlorophenyl)-5-{4-[3-(2-hydroxyacetylamino)propoxy]-phenyl}-1-methyl-1H-pyrrole-2-carbonyl)-[1',4]bipiperidinyl-4'-carboxamide | 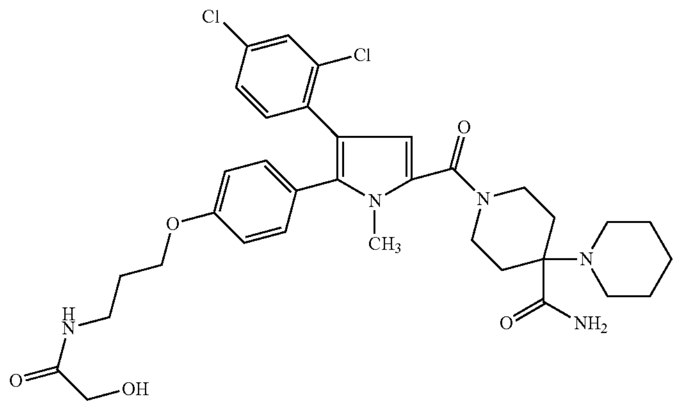 [SMILES: Cn1c(C(=O)N2CCC(C(N)=O)(N3CCCCC3)CC2)cc(-c2ccc(Cl)cc2Cl)c1-c1ccc(OCCCNC(=O)CO)cc1] |
| 1'-[4-(2,4-dichlorophenyl)-5-[4-(3-hydroxpropoxy)phenyl]-1-methyl-1H-pyrrole-2-carbonyl]-[1',4]bipiperidinyl-4'-carboxamide | 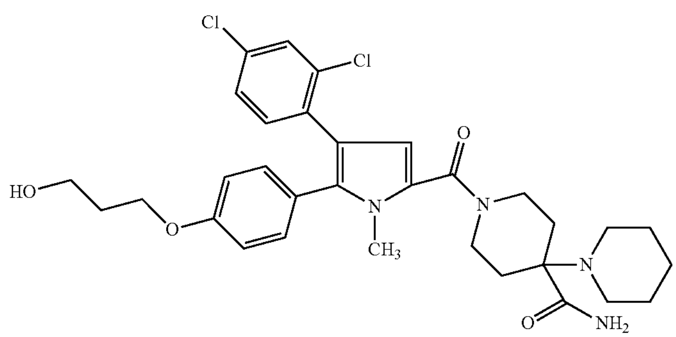 [SMILES: Cn1c(C(=O)N2CCC(C(N)=O)(N3CCCCC3)CC2)cc(-c2ccc(Cl)cc2Cl)c1-c1ccc(OCCCO)cc1] |
| 1'-[4-(2,4-dichlorophenyl)-5-[4-(3-methanesulphonylaminopropoxy)-phenyl]-1-methyl-1H-pyrrole-2-carbonyl]-4,4-difluoro-[1,4']bipiperidinyl-4'-carboxamide | 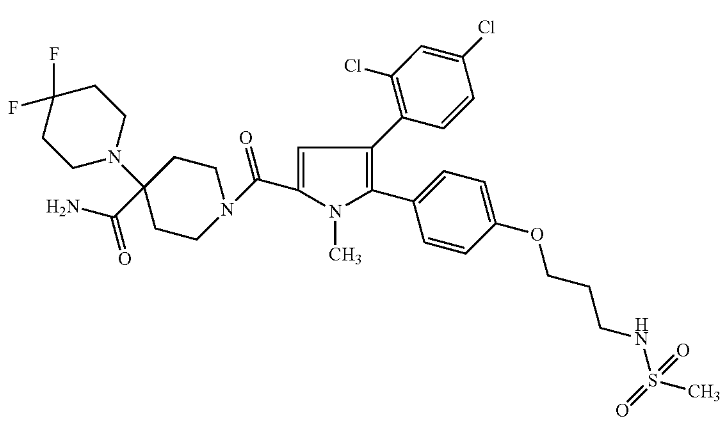 [SMILES: Cn1c(C(=O)N2CCC(C(N)=O)(N3CCC(F)(F)CC3)CC2)cc(-c2ccc(Cl)cc2Cl)c1-c1ccc(OCCCNS(C)(=O)=O)cc1] |

-continued

| IUPAC Name | Chemical Structure |
|---|---|
| 1'-[4-(2,4-dichlorophenyl)-5-(4-(3-methylaminopropoxy)phenyl)-1-methyl-1H-pyrrole-2-carbonyl]-[1,4']bipiperidinyl-4'-carboxamide | 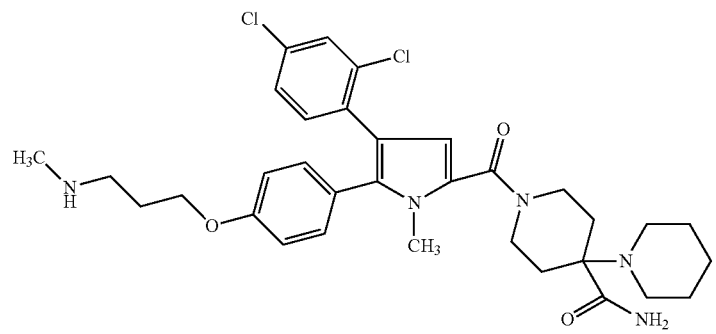 [SMILES: CNCCCOc1ccc(-c2c(-c3ccc(Cl)cc3Cl)cc(C(=O)N3CCC(C(N)=O)(N4CCCCC4)CC3)n2C)cc1] |
| 1'-[4-(2,4-dichlorophenyl)-1-methyl-5-[4-(3-pyrrolidin-1-yl-propoxy)-phenyl]-1H-pyrrole-2-carbonyl]-[1,4']bipiperidinyl-4'-carboxamide | 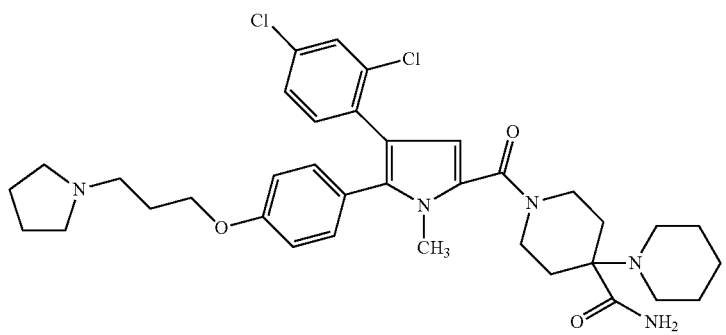 [SMILES: Cn1c(C(=O)N2CCC(C(N)=O)(N3CCCCC3)CC2)cc(-c2ccc(Cl)cc2Cl)c1-c1ccc(OCCCN2CCCC2)cc1] |
| 1-[4-(2,4-dichlorophenyl)-5-(4-(3-hydroxypropoxy)phenyl)-1-methyl-1H-pyrrole-2-carbonyl]-4-phenylpiperidine-4-carboxamide | 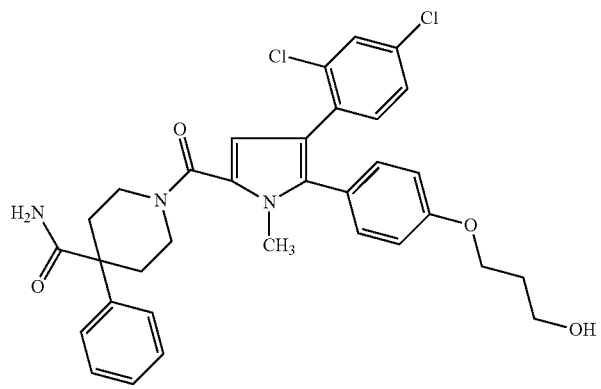 [SMILES: Cn1c(C(=O)N2CCC(C(N)=O)(c3ccccc3)CC2)cc(-c2ccc(Cl)cc2Cl)c1-c1ccc(OCCCO)cc1] |
| 1-[4-(2,4-dichlorophenyl)-5-[4-(3-hydroxypropoxy)phenyl]-1-methyl-1H-pyrrole-2-carbonyl]-4-(3-fluorobenzylamino)piperidine-4-carboxamide | 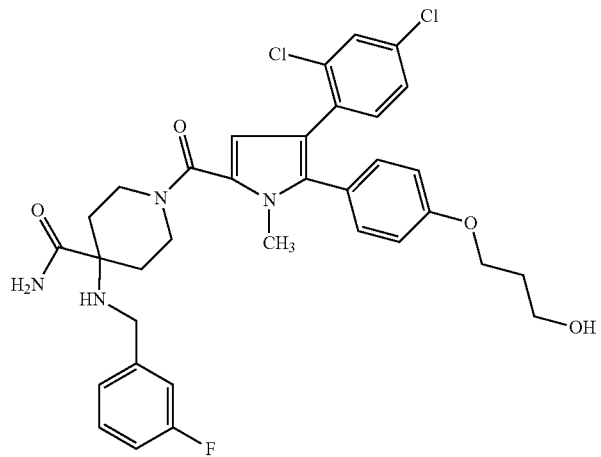 [SMILES: Cn1c(C(=O)N2CCC(NCc3cccc(F)c3)(C(N)=O)CC2)cc(-c2ccc(Cl)cc2Cl)c1-c1ccc(OCCCO)cc1] |

-continued

| IUPAC Name | Chemical Structure |
|---|---|
| 1-[4-(2,4-dichlorophenyl)-5-[4-(2-hydroxyethoxy)phenyl]-1-methyl-1H-pyrrole-2-carbonyl]-4-phenyl-piperidine-4-carboxamide | 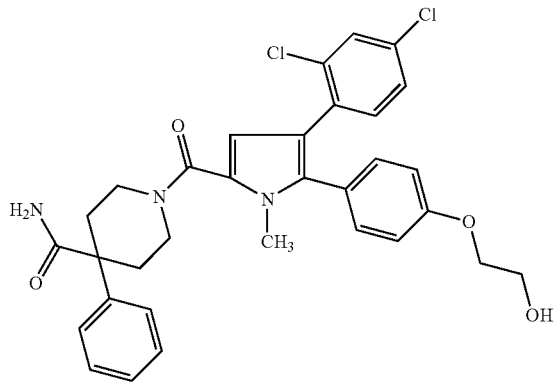 [SMILES: Cn1c(C(=O)N2CCC(C(N)=O)(c3ccccc3)CC2)cc(-c2ccc(Cl)cc2Cl)c1-c1ccc(OCCO)cc1] |
| 1-[4-(2,4-dichlorophenyl)-5-[4-(2-hydroxyethoxy)phenyl]-1-methyl-1H-pyrrole-2-carbonyl]-4-(3-fluoro-benzylamino)piperidine-4-carboxamide | 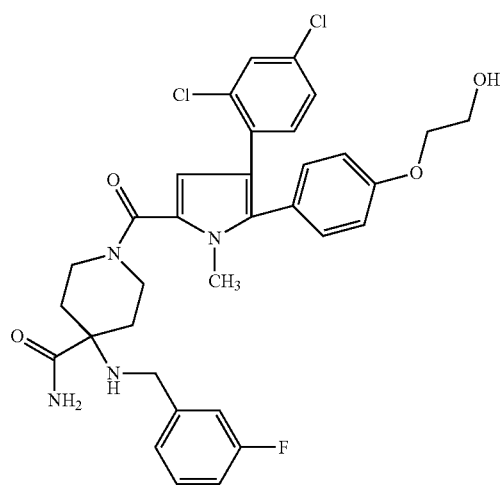 [SMILES: Cn1c(C(=O)N2CCC(NCc3cccc(F)c3)(C(N)=O)CC2)cc(-c2ccc(Cl)cc2Cl)c1-c1ccc(OCCO)cc1] |
| 1-[5-[4-(3-carbamoylpropoxy)-phenyl]-4-(2,4-dichlorophenyl)-1-methyl-1H-pyrrole-2-carbonyl]-4-[(3-fluorophenylamino)-methyl]piperidine-4-carboxamide | 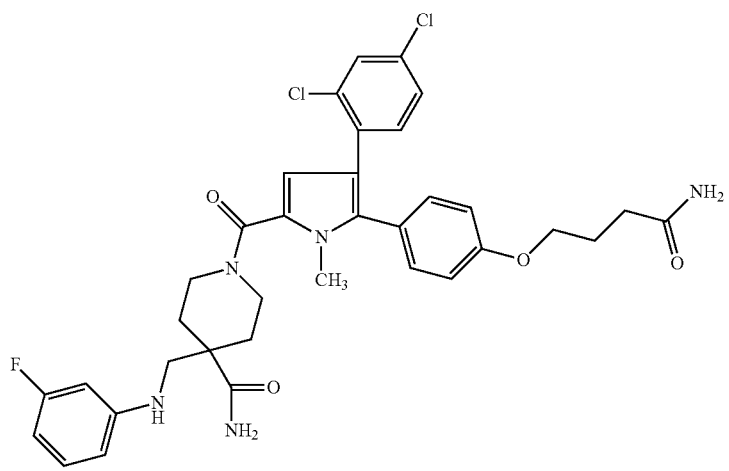 [SMILES: Cn1c(C(=O)N2CCC(CNc3cccc(F)c3)(C(N)=O)CC2)cc(-c2ccc(Cl)cc2Cl)c1-c1ccc(OCCCC(N)=O)cc1] |

| IUPAC Name | Chemical Structure |
|---|---|
| 1-[5-[4-(3-carbamoylpropoxy)-phenyl]-4-(2,4-dichlorophenyl)-1-methyl-1H-pyrrole-2-carbonyl]-4-phenylpiperidine-4-carboxamide | 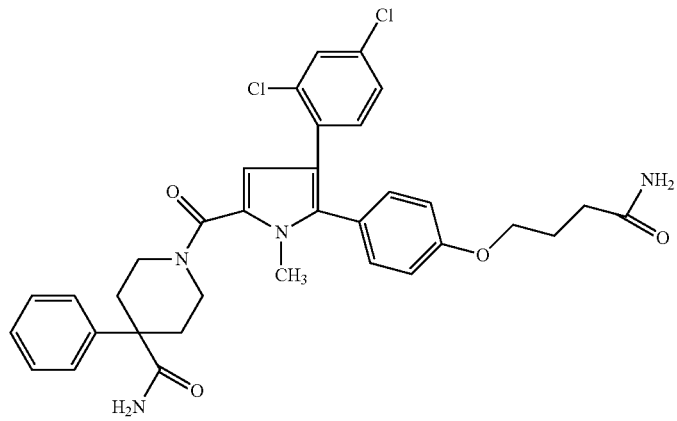 [SMILES: Cn1c(C(=O)N2CCC(C(N)=O)(c3ccccc3)CC2)cc(-c2ccc(Cl)cc2Cl)c1-c1ccc(OCCCC(N)=O)cc1] |
| 1-[5-(4-carbamoylmethoxy)phenyl-4-(2,4-dichlorophenyl)-1-methyl-1H-pyrrole-2-carbonyl]-4-phenylpiperidine-4-carboxamide | 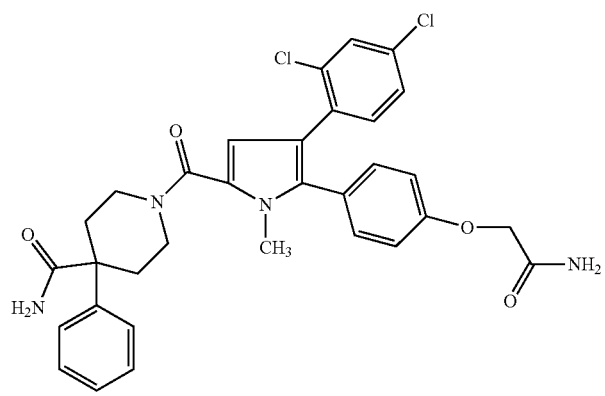 [SMILES: Cn1c(C(=O)N2CCC(C(N)=O)(c3ccccc3)CC2)cc(-c2ccc(Cl)cc2Cl)c1-c1ccc(OCC(N)=O)cc1] |
| Trifluoroacetic acid salt of 1-[5-(4-carbamoylmethoxyphenyl)-4-(2,4-dichlorophenyl)-1-methyl-1H-pyrrole-2-carbonyl]-4-(4-fluorobenzylamino)-piperidine-4-carboxamide | 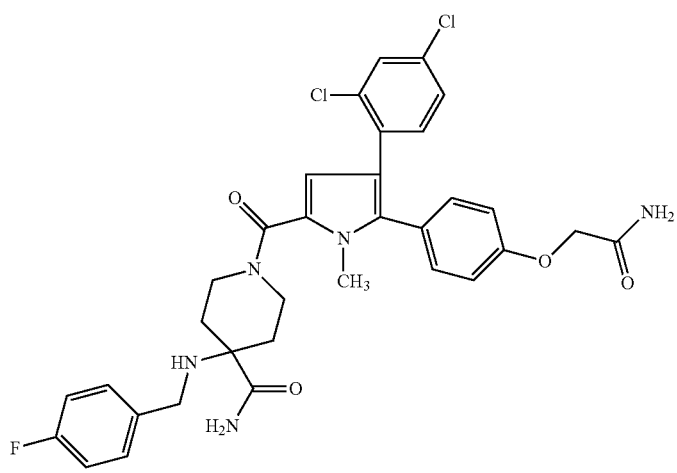 [SMILES: Cn1c(C(=O)N2CCC(NCc3ccc(F)cc3)(C(N)=O)CC2)cc(-c2ccc(Cl)cc2Cl)c1-c1ccc(OCC(N)=O)cc1] |

-continued

| IUPAC Name | Chemical Structure |
|---|---|
| 4-(4-chlorophenyl)-1-[4-(2,4-dichlorophenyl)-5-[4-(2-hydroxyethoxy)phenyl]-1-methyl-1H-pyrrole-2-carbonyl]piperidine-4-carboxamide | 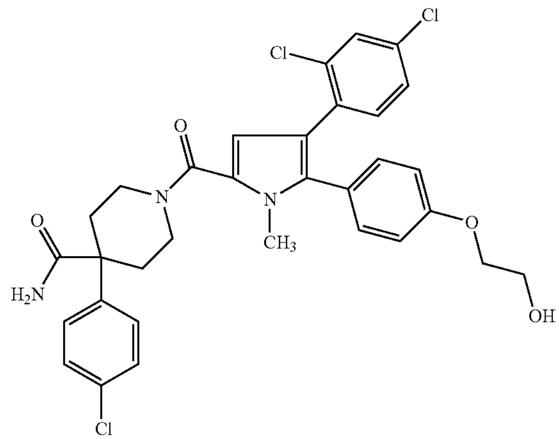 [SMILES: Cn1c(C(=O)N2CCC(C(N)=O)(c3ccc(Cl)cc3)CC2)cc(-c2ccc(Cl)cc2Cl)c1-c1ccc(OCCO)cc1] |
| 1-[4-(2,4-dichlorophenyl)-5-[4-(2-hydroxyethoxy)phenyl]-1-methyl-1H-pyrrole-2-carbonyl]-4-(4-fluoro-benzylamino)piperidine-4-carboxamide | 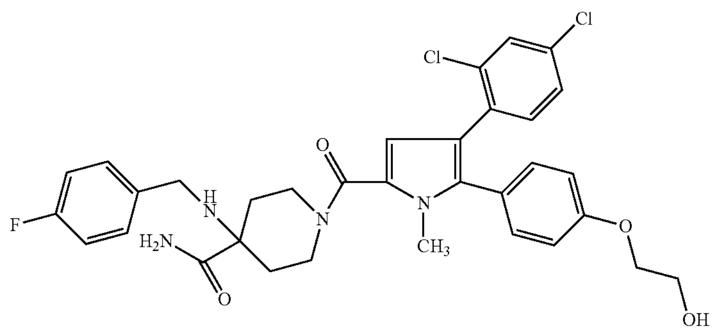 [SMILES: Cn1c(C(=O)N2CCC(NCc3ccc(F)cc3)(C(N)=O)CC2)cc(-c2ccc(Cl)cc2Cl)c1-c1ccc(OCCO)cc1] |
| 1-[4-(2-chlorophenyl)-5-[4-(2-hydroxyethoxy)phenyl]-1-methyl-1H-pyrrole-2-carbonyl]-4-(4-fluoro-benzylamino)piperidine-4-carboxamide | 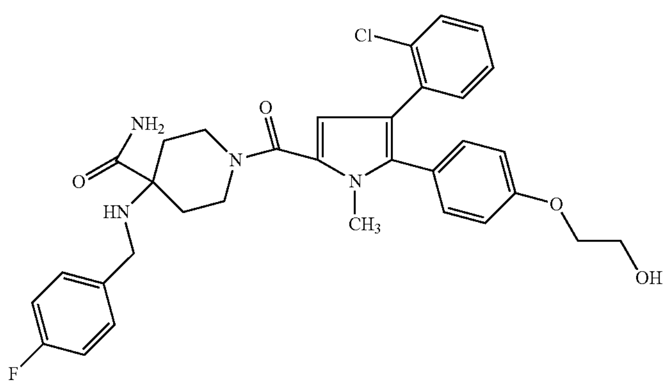 [SMILES: Cn1c(C(=O)N2CCC(NCc3ccc(F)cc3)(C(N)=O)CC2)cc(-c2ccccc2Cl)c1-c1ccc(OCCO)cc1] |
| 4-(4-chlorophenyl)-1-[4-(2-chlorophenyl)-5-[4-(2-hydroxyethoxy)phenyl]-1-methyl-1H-pyrrole-2-carbonyl]piperidine-4-carboxamide | 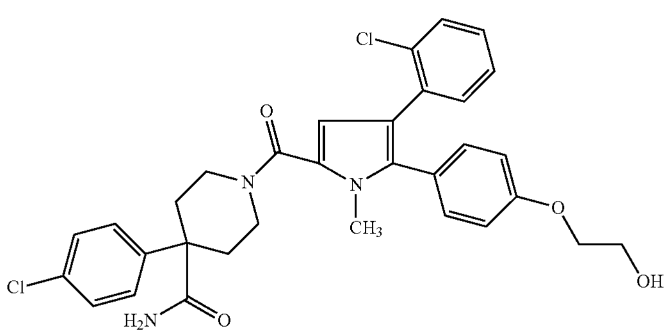 [SMILES: Cn1c(C(=O)N2CCC(C(N)=O)(c3ccc(Cl)cc3)CC2)cc(-c2ccccc2Cl)c1-c1ccc(OCCO)cc1] |

| IUPAC Name | Chemical Structure |
|---|---|
| 4-benzylamino-1-[4-(2-chlorophenyl)-5-[4-(2-hydroxyethoxy)phenyl]-1-methyl-1H-pyrrole-2-carbonyl]piperidine-4-carboxamide | 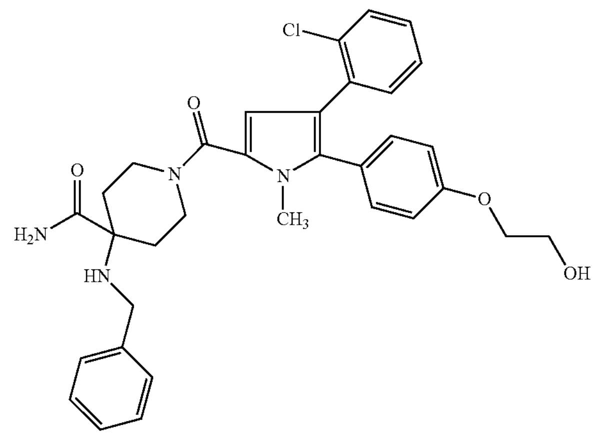 [SMILES: Cn1c(C(=O)N2CCC(NCc3ccccc3)(C(N)=O)CC2)cc(-c2ccccc2Cl)c1-c1ccc(OCCO)cc1] |
| 1-[4-(2-chlorophenyl)-5-[4-(2-hydroxyethoxy)phenyl]-1-methyl-1H-pyrrole-2-carbonyl]-4-(3-fluorobenzylamino)piperidine-4-carboxamide | |
| 1-[4-(2-chlorophenyl)-5-[4-(3-hydroxypropoxy)phenyl]-1-methyl-1H-pyrrole-2-carbonyl]-4-(4-fluorobenzylamino)piperidine-4-carboxamide | |
| 4-benzylamino-1-[4-(2-chlorophenyl)-5-[4-(3-hydroxypropoxy)phenyl]-1-methyl-1H-pyrrole-2-carbonyl]piperidine-4-carboxamide | 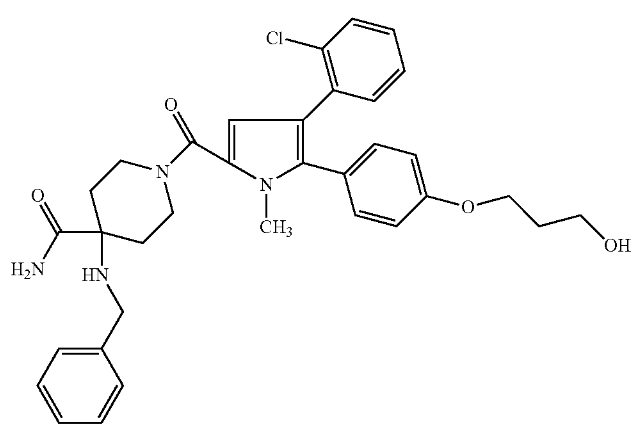 [SMILES: Cn1c(C(=O)N2CCC(NCc3ccccc3)(C(N)=O)CC2)cc(-c2ccccc2Cl)c1-c1ccc(OCCCO)cc1] |

| IUPAC Name | Chemical Structure |
| --- | --- |
| 4-(4-chlorophenyl)-1-[4-(2-chlorophenyl)-5-[4-(3-hydroxypropoxy)phenyl]-1-methyl-1H-pyrrole-2-carbonyl]piperidine-4-carboxamide | |
| 1-[4-(2-chlorophenyl)-5-[4-(3-hydroxypropoxy)phenyl]-1-methyl-1H-pyrrole-2-carbonyl]-4-(3-fluorobenzylamino)piperidine-4-carboxamide | |
| 1-[5-(4-carbamoylmethoxyphenyl)-4-(2-chlorophenyl)-1-methyl-1H-pyrrole-2-carbonyl]-4-(4-fluorobenzylamino)piperidine-4-carboxamide | |
| 1-[5-(4-carbamoylmethoxyphenyl)-4-(2-chlorophenyl)-1-methyl-1H-pyrrole-2-carbonyl]-4-(3-fluorobenzylamino)piperidine-4-carboxamide | |

Among the compounds listed above, the following are preferred:

1-[4-(2,4-dichlorophenyl)-5-[4-(3-hydroxypropoxy)phenyl]-1-methyl-1H-pyrrole-2-carbonyl]-4-(3-fluorobenzylamino)piperidine-4-carboxamide, 1-[5-(4-carbamoylmethoxy)phenyl-4-(2,4-dichlorophenyl)-1-methyl-1H-pyrrole-2-carbonyl]-4-phenylpiperidine-4-carboxamide, 1-[4-(2-chlorophenyl)-5-[4-(3-hydroxypropoxy)phenyl]-1-methyl-1H-pyrrole-2-carbonyl]-4-(4-fluorobenzylamino)piperidine-4-carboxamide, and the salts thereof.

A subject of the present invention is also a process for preparing the compounds according to the invention.

This process is characterized in that:

the acid of Formula (II) or a functional derivative of this acid of Formula (II):

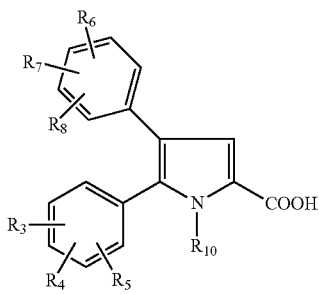

(II)

in which $R_3$, $R_4$, $R_5$, $R_6$, $R_7$, $R_8$ and $R_{10}$ are as defined for (I), is treated with an amine of Formula $HNR_1R_2$ in which $R_1$ and $R_2$ are as defined for (I).

The compounds of Formula (I) obtained by means of the various protocols can be subsequently separated from the reaction medium and purified according to conventional methods, for example by crystallization or chromatography.

Optionally, the compound of Formula (I) thus obtained is converted to a salt thereof.

As functional derivative of the acid (II), use may in particular be made of the acid chloride, the anhydride, a mixed anhydride, a $C_1$-$C_4$ alkyl ester in which the alkyl is unbranched or branched, a benzyl ester, an activated ester, for example the ester of p-nitrophenyl, or the free acid opportunely activated, for example, with N,N-dicyclohexylcarbodiimide or with benzotriazol-1-yloxo-tris(dimethylamino) phosphonium hexafluorophosphate (BOP) or benzotriazol-1-yloxotris(pyrrolidino)phosphonium hexafluorophosphate (PyBOP) or N—[N-(dimethylamino)-1-1,2,3-triazolo[4,5-b] pyridin-1-ylmethylene]-N-methylmethanaminium hexafluorophosphate N-oxide (HBTU). These functional derivatives of the acid (II) correspond to the compounds (11.1).

Thus, in the process according to the invention, the chloride of the acid of Formula (II), obtained by reaction of thionyl chloride or of 1-chloro-N,N-2-trimethyl-1-propene-1-amine, carried out according to Chem. Comm., 1988, 475-477, at 0° C., on the acid of Formula (II), with an amine $HNR_1R_2$, in an inert solvent, such as for example a chlorinated solvent (dichloromethane, dichloroethane or chloroform, for example), an ether (tetrahydrofuran or dioxane, for example) or an amide (N,N-dimethylformamide, for example) under an inert atmosphere, at a temperature of between 0° C. and AT, in the presence of a tertiary amine such as, for example, triethylamine, N-methylmorpholine or pyridine.

One variant consists in preparing the mixed anhydride of the acid of Formula (II) by reaction of ethyl chloroformate with the acid of Formula (II), in the presence of a base such as, for example, triethylamine, and in reacting it with an amine $HNR_1R_2$, in a solvent such as, for example, dichloromethane, under an inert atmosphere, at AT, in the presence of a base such as triethylamine.

The compounds of Formula (II) can be prepared according to Scheme 1 below. For this method of preparation, the chemical group $Y$-$A$-$R_9$ is:

either present within the compound (V); in this case, $R_3$ represents the $Y$-$A$-$R_9$ group;

or present within the compound (VIII); in this case, $R_6$ represents the $Y$-$A$-$R_9$ group.

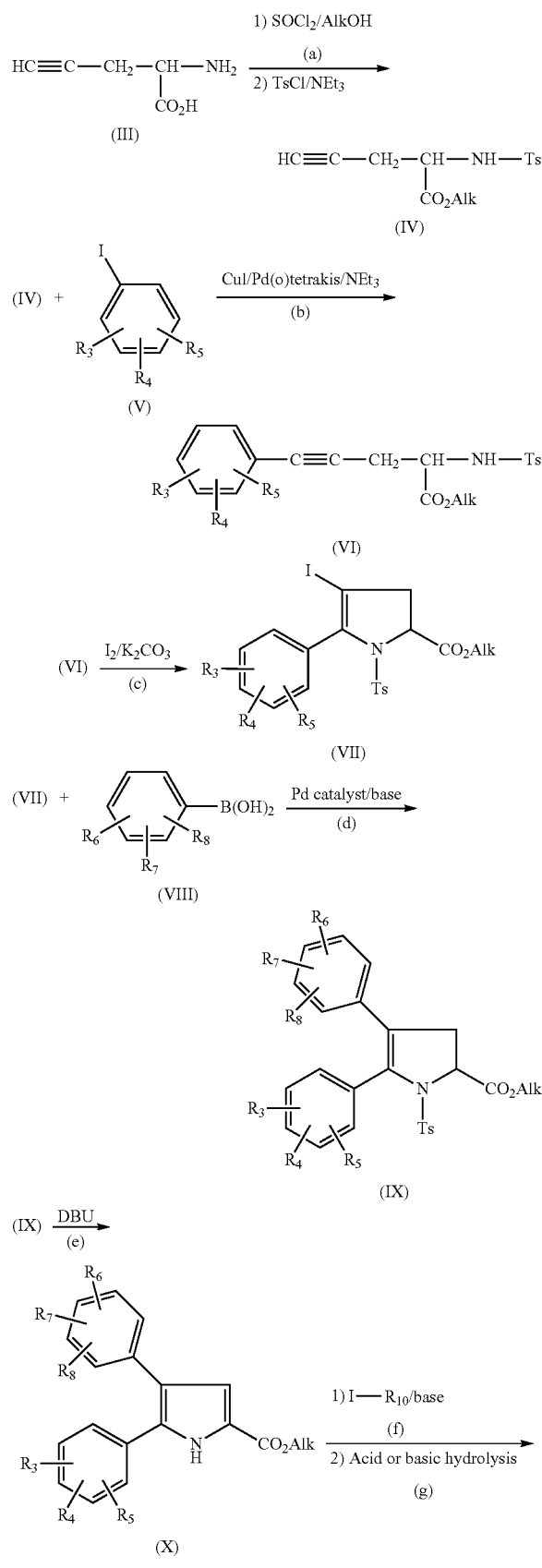

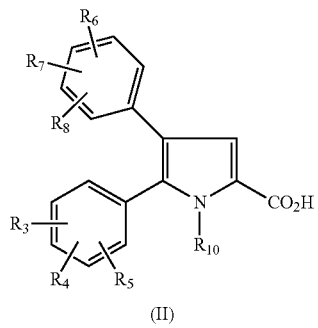

(II)

The preparation of the dihydropyrrole derivative of Formula (VII) via stages a), b) and c) is carried out according to J. Chem. Soc. Perkin Trans. 1, 2002, 622-628. The alkyl group Alk corresponds to a ($C_1$-$C_4$)alkyl group and the Ts group corresponds to a protective group, such as, for example, the tosyl radical of Formula —$SO_2$—$C_6H_4$—$CH_3$.

The substitution of the dihydropyrrole nucleus with a substituted phenyl group is carried out in stage d) through the action of a substituted phenylboronic acid of Formula (VIII) in the presence of a palladium catalyst such as, for example, tetrakis(triphenylphosphine)Pd(0), palladium(0) bisdibenzylidene acetone [Pd(dba)$_2$], tris(dibenzylideneacetone)dipalladium(0), palladium acetate Pd(II)[Pd(OCOCH$_3$)$_2$], or dichloro(diphenylphosphinoferrocene) Pd(II) [PdCl$_2$dppf], and in the presence of a base such as, for example, sodium carbonate.

In stage e), the protection of the nitrogen with the Ts group is removed through the action of a diamine such as, for example, DBU (1,8-diazabicyclo[5.4.0]undecene) and the dihydropyrrole nucleus is simultaneously aromatized.

The compound of Formula (X) is subsequently treated with an iodide of Formula $R_{10}$—I in the presence of a base such as, for example, potassium carbonate and in DMF, so as to give, in stage f), a compound of Formula (XI).

In stage g) the compound of Formula (XI) is hydrolysed in an acidic or basic medium. The acid (II) thus formed is treated with the amine $HNR_1R_2$ so as to form the compound (I) according to the invention.

Alternatively, the compounds of Formula (I) can be obtained from the acids of Formula (IIa) and (IIa') in which $R_3$, $R_4$, $R_5$, $R_6$, $R_7$, $R_8$ and $R_{10}$ are as defined for (I) and the Y-A-$R_9$ group is replaced with a group Z which is a chemical precursor of the Y-A-$R_9$ group.

The term "group Z" is intended to mean chemical groups which, after one or more reaction stages known to those skilled in the art, give the groups Y-A-$R_9$. For example, the precursor group Z corresponds to Y—H, a halogen atom, or a Y-A-OH, Y-A-Cl, Y-A-$CO_2$Alk or Y-A-NHPg group.

Thus, according to Scheme 2 below, the acid of Formula (IIa) in which $R_6$ is replaced with the group Z is used as starting point. This acid is treated with an amine of Formula $HNR_1R_2$, $R_1$ and $R_2$ being as defined for (I). An amide of Formula (Ia) is obtained.

The group Z of the compound of Formula (Ia) obtained is then converted, in one or more stages, to the Y-A-$R_9$ group by one of the methods known to those skilled in the art, so as to give the compounds of Formula (I).

Scheme 2

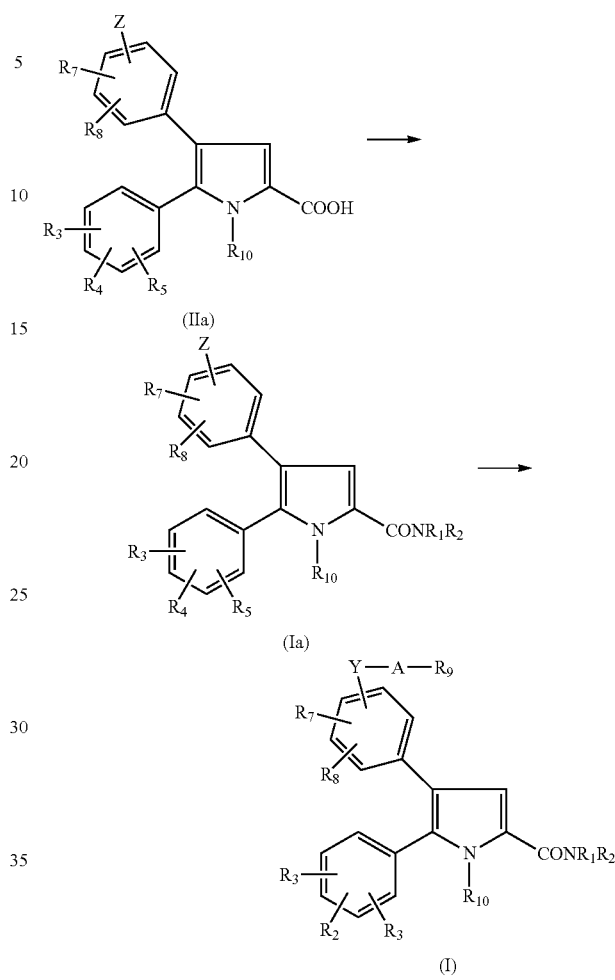

Alternatively, according to Scheme 2' below, the acid of Formula (IIa') in which $R_3$ is replaced with the group Z is used as starting point. This acid is treated with an amine of Formula $HNR_1R_2$, $R_1$ and $R_2$ being as defined for (I). An amide of Formula (Ia') is obtained.

The group Z of the compound of Formula (Ia') obtained is then converted, in one or more stages, to the Y-A-$R_9$ group by one of the methods known to those skilled in the art, so as to give the compounds of Formula (I).

Scheme 2'

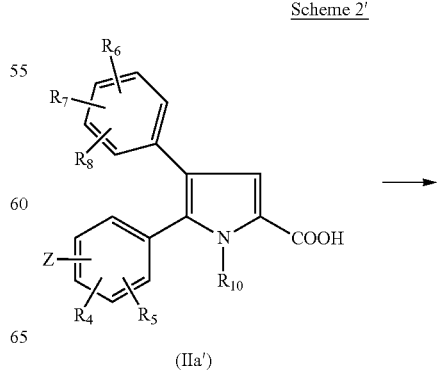

(IIa')

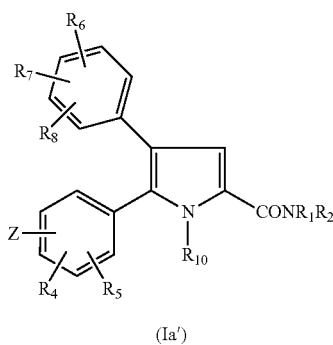

(Ia')

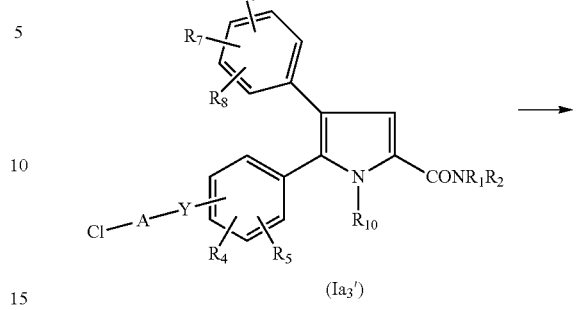

(Ia₃')

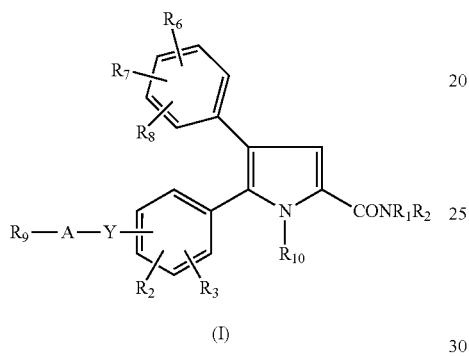

(I)

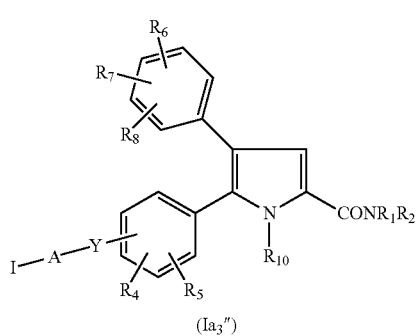

(Ia₃")

By way of examples, the compounds of Formula (I) in which Y corresponds to an oxygen or sulphur atom and $R_9$ represents an $NR_{12}R_{13}$ group can be obtained from a compound of Formula (Ia') in which $R_3$ is replaced with Z, and Z corresponds to YH.

According to Scheme 3, the compound (Ia') is treated with a dihalogenated derivative of Formula Cl-A-Br so as to obtain a compound of Formula (Ia₃') in which Z has become Y-A-Cl.

The compound of Formula (Ia₃') obtained is then treated with sodium iodide, forming a compound of Formula (Ia₃") containing the Y-A-I group.

The compound of Formula (Ia₃') is subsequently reacted with an amine of Formula $NHR_{12}R_{13}$ so as to obtain the compound of Formula (I) in which Y-A-$R_9$ corresponds to Y-A-$NR_{12}R_{13}$.

Scheme 3

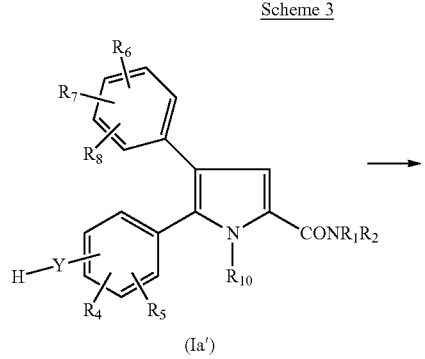

(Ia')

(Ia₃") →

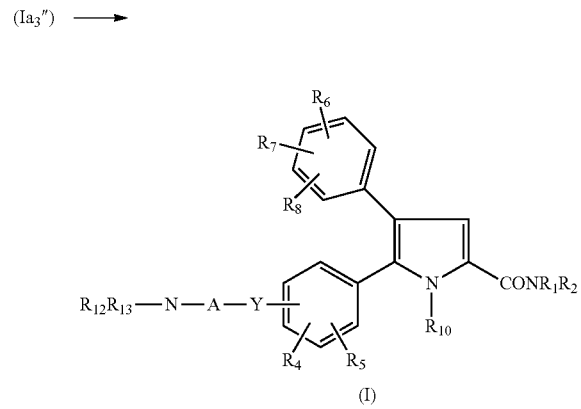

(I)

Similarly, the compounds of Formula (I) in which Y corresponds to an oxygen or sulphur atom and $R_9$ represents a $CONR_{12}R_{13}$ group can be obtained from this same compound of Formula (Ia'). According to Scheme 4, the compound of Formula (Ia') is alkylated with a halogenated derivative of Formula Br-A-CO₂Alk so as to obtain a compound of Formula (Ia4') in which Z has become Y-A-CO₂Alk.

This compound of Formula (Ia4') is subsequently saponified according to the methods known to those skilled in the art, so as to give the compound of Formula (Ia4") containing the Y-A-CO₂H group.

After activation of the acid of the compound of Formula (Ia4") with carbonyldiimidazole, reaction with ammonia makes it possible to obtain the compound of Formula (I) in which Y-A-$R_9$ corresponds to Y-A-CONH₂.

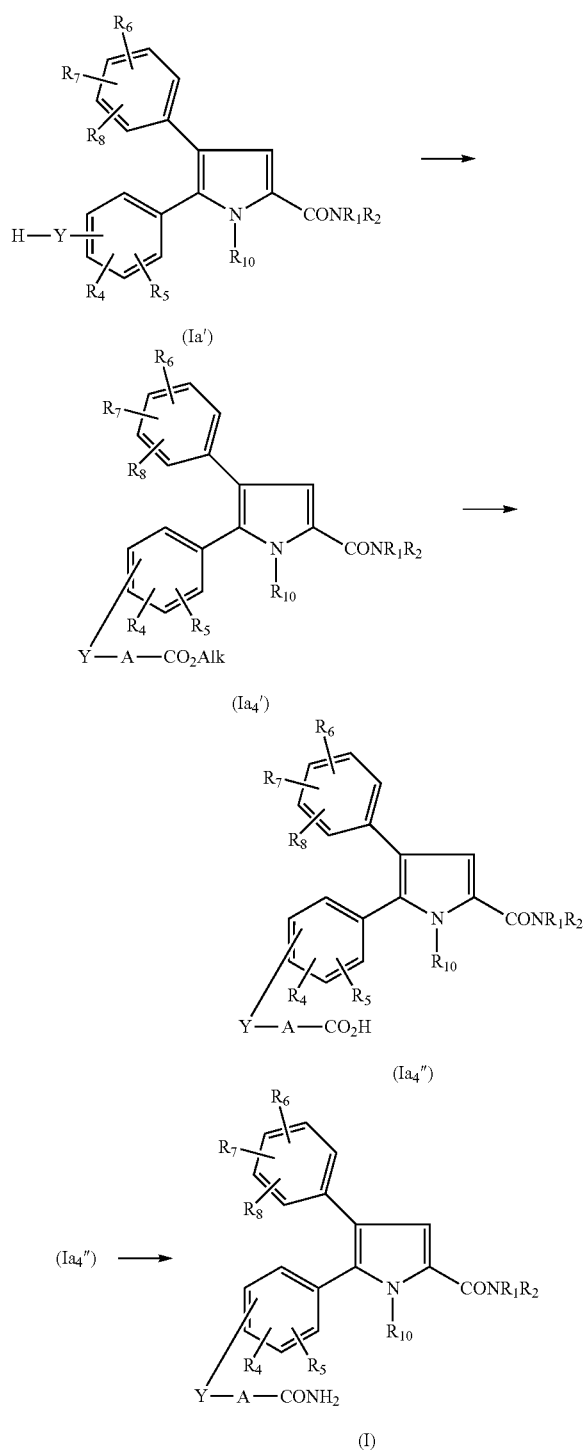

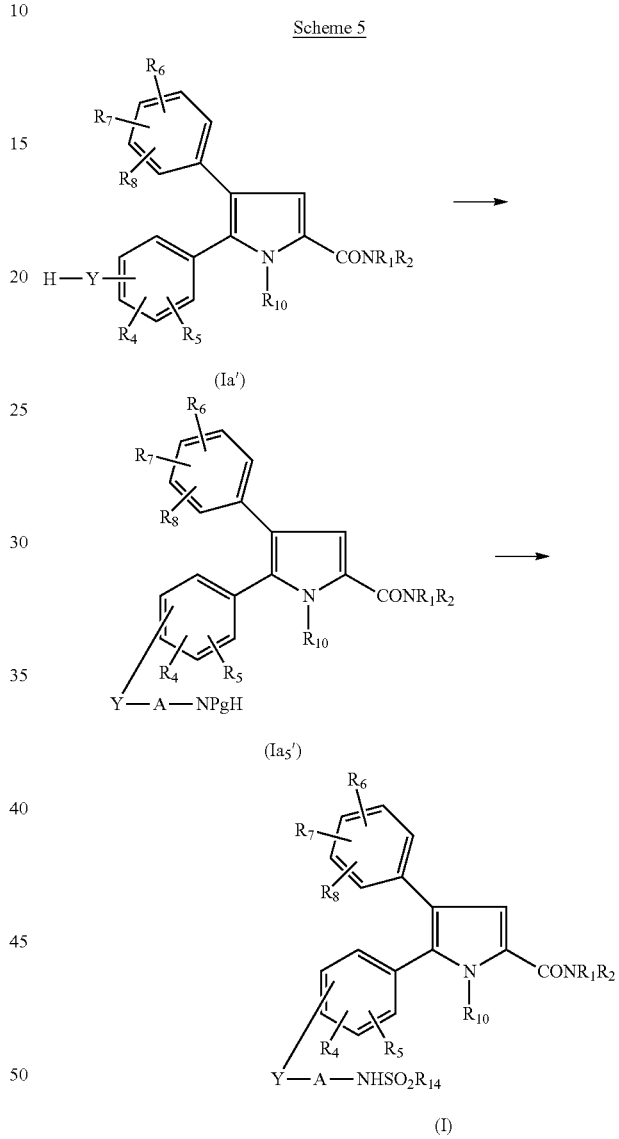

The compound of Formula (Ia') also makes it possible to produce compounds of Formula (I) in which Y corresponds to an oxygen or sulphur atom and $R_9$ represents an $NHSO_2R_{14}$ group.

According to Scheme 5, the compound of Formula (Ia') is, in this case, alkylated with a halogenated derivative of Formula Br-A-NPgH so as to obtain a compound of Formula (Ia5') in which Z has become Y-A-NPgH, Pg being an amine-function-protecting group, for example tert-butyloxycarbonyl. Other examples of protective groups Pg are given in "Protective Group in Organic Synthesis", Green et al, 4th edition, John Wiley & Sons, Inc., New York, 2007.

The compound of Formula (I) in which Y-A-$R_9$ corresponds to Y-A-$NHSO_2R_{14}$ is obtained by deprotection of the amine, followed by reaction with the alkylsulphonyl chloride of Formula $ClSO_2R_{14}$.

By way of examples concerning the preparation of compounds of Formula (I) in which $R_6$ corresponds to Y-A-$NR_{12}R_{13}$, Y-A-$CO_2H$, Y-A-$CONH_2$ or Y-A-$NHSO_2R_{14}$, the compounds of Formula (Ia) with the reaction Schemes 3, 4 and 5 indicated above being applied thereto.

The acids (IIa) and (IIa') are prepared in the same way as the acids (II) according to reaction Scheme 1.

In order to prepare the acid of Formula (IIa) or (IIa') with Z corresponding to Y—H, the acid of Formula (IIa) or (IIa') in which Z is replaced with Y—$CH_3$ is reacted with $BBr_3$, in a solvent such as, for example, dichloromethane and at a temperature of between −20° C. and 0° C.

The amines of Formula $HNR_1R_2$ are known or prepared by known methods, for example those described in J. Med. Chem., 7, 1964, 619-622, or in J. Org. Chem., 55, 1990, 4207-4209.

A subject of the present invention is also the compounds of Formula (II) and the functional derivatives thereof of Formula (II.1). Among these compounds of Formulae (II) and (II.1), those which in particular stand out are those of Formula (II.2) corresponding to the formula:

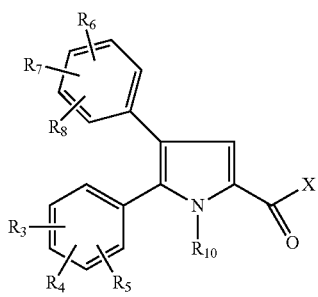

in which:
- X represents a hydroxyl group, a halogen atom, $(C_1\text{-}C_4)$ alkoxy or benzyloxy;
- and $R_3$, $R_4$, $R_5$, $R_6$, $R_7$, $R_8$ and $R_{10}$ are as defined for the compounds of Formula (I).

Thus, in order to prepare a compound of Formula (I) according to the invention, the compound of Formula (II.2) is treated with, in particular, an amine of Formula $HNR_1R_2$ in which $R_1$ and $R_2$ are as defined for the compounds of Formula (I).

The following examples describe the preparation of some compounds in accordance with the invention. These examples are not limiting and merely illustrate the present invention. The numbers of the compounds exemplified refer back to those given in the table hereinafter, which illustrates the chemical structures and the physical properties of some compounds according to the invention.

In the examples, the following abbreviations are used:
EtOAc: Ethyl acetate
$NH_4OAc$: ammonium acetate
DCM: Dichloromethane
DIPEA: Diisopropylethylamine
DMF: N,N-dimethylformamide.
HBTU: N-[N-(dimethylamino)-1H-1,2,3-triazolo[4,5-b]pyridin-1-ylmethylene]-N-methylmethanaminium hexafluorophosphate N-oxide]
HOBt: 1-hydroxybenzotriazole
HPLC: High-pressure liquid chromatography
MeOH: Methanol
Ammoniacal methanol: 7N $NH_3$ in solution in MeOH
PyBOP: benzotriazol-1-yloxotris(pyrrolidino)phosphonium hexafluorophosphate
AT: Ambient Temperature
Mp: Melting point
TFA: Trifluoroacetic Acid
THF: Tetrahydrofurane
UPLC: Ultra Performance Liquid Chromatography The nuclear magnetic resonance spectra are recorded at 200 MHz or 250 MHz in DMSO-d6. The following abbreviations are used for the interpretation of the spectra: s: singulet, d: doublet, t: triplet, q: quadruplet, qui: quintuplet, m: unresolved peak, bs: broad singlet, dd: doublet of doublet.

The compounds according to the invention are analysed by LC/UV/MS coupling (liquid chromatography/UV detection/mass spectrometry). The characteristic molecular peak ($MH^+$) and the retention time (tr) in minutes (min) are measured.

The compounds are analysed by HPLC-UV-MS or alternatively UPLC-UV-MS (liquid chromatography-UV detection and mass detection) coupling.

The analytical conditions are the following:
Conditions A (HPLC):
Use is made of a column: Symmetry C18 (50×2.1 mm; 3.5 µm)
Eluent A: 0.005% of trifluoroacetic acid (TFA) in water at approximately pH 3.1
Eluent B: 0.005% of TFA in acetonitrile.
Gradient:

| Time (min) | % A | % B |
|---|---|---|
| 0 | 100 | 0 |
| 10 | 10 | 90 |
| 15 | 10 | 90 |
| 16 | 100 | 0 |
| 20 | 100 | 0 |

Column temperature: 30° C.; flow rate: 0.4 ml/minute.
Detection: λ=210 nm–220 nm
Conditions B (HPLC):
Use is made of an XTerra MS C18 column (50×2.1 mm; 3.5 µm)
Eluent A: 10 mM $NH_4OAc$ at approximately pH 7
Eluent B: acetonitrile
Gradient:

| Time (min) | % A | % B |
|---|---|---|
| 0 | 100 | 0 |
| 10 | 10 | 90 |
| 15 | 10 | 90 |
| 16 | 100 | 0 |
| 20 | 100 | 0 |

Column temperature: 30° C.; flow rate: 0.4 ml/minute.
Detection: λ=220 nm
Conditions C (UPLC):
Use is made of an Acquity BEH C18 column (50×2.1 mm; 1.7 µm)
Eluent A: 0.005% of TFA in water at approximately pH 3.1/acetonitrile (97/3)
Eluent B: 0.035% of TFA in acetonitrile.
Gradient:

| Time (min) | % A | % B |
|---|---|---|
| 0 | 100 | 0 |
| 2.3 | 5 | 95 |
| 2.9 | 5 | 95 |
| 3 | 100 | 0 |
| 3.5 | 100 | 0 |

Column temperature: 40° C.; flow rate: 1 ml/minute.
Detection: λ=220 nm
Conditions D (UPLC):
Use is made of an Acquity BEH C18 column (50×2.1 mm; 1.7 µm)
Eluent A: 0.005% of TFA in water at approximately pH 3.1/acetonitrile (97/3)
Eluent B: 0.035% of TFA in acetonitrile.

Gradient:

| Time (min) | % A | % B |
|---|---|---|
| 0 | 100 | 0 |
| 4.8 | 5 | 95 |
| 6 | 5 | 95 |
| 6.1 | 100 | 0 |
| 6.6 | 100 | 0 |

Column temperature: 40° C.; flow rate: 1 ml/minute.
Detection: λ=220 nm
Mass Spectrometry Conditions:

The mass spectra are recorded in positive electrospray mode (ESI), in order to observe the ions derived from the protonation of analysed compounds ($MH^+$), or from the formation of adducts with other cations, such as $Na^+$, $K^+$, etc.

Preparations
Preparation 1:

Ethyl 4-(2,4-dichlorophenyl)-5-(4-hydroxyphenyl)-1-methyl-1H-pyrrole-2-carboxylate

1a) 2-(((4-methylphenyl)sulphonyl)amino)pent-3-ynoic acid ethyl ester 2.5 g of 2-aminobut-3-ynoic acid are suspended in 45 ml of ethyl at 0° C. 1.8 ml of thionyl chloride are run in, dropwise, at this temperature, and the mixture is then brought to reflux for 3 hours. The solution is concentrated and the residue is dried under reduced pressure. The latter is solubilized in 60 ml of acetonitrile followed by 5.4 ml of triethylamine, and then 4.6 g of tosyl chloride are added. The mixture is stirred at AT for 19 hours, and then at 50° C. for a further hour. After concentration, the crude product is solubilized in dichloromethane, and the organic phase is washed successively with a saturated aqueous solution of $KHSO_4$ and then of $K_2CO_3$. The organic phase is dried over magnesium sulphate, then filtered and, finally, concentrated so as to obtain 5.18 g of the expected compound.

$^1H$ NMR, (200 MHz): δ (ppm): 1.13: t: 3H; 2.35: s: 3H; 2.45: m: 2H; 3.69-4.05: m: 3H; 7.35: d: 2H; 7.65: d: 2H; 8.4: d: 1H.

1b) 5-(4-methoxyphenyl)-2-(4-tosylsulphonylamino)pent-4-ynoic acid ethyl ester 40 g of the compound of the preceding stage 1a) and 31.7 g of iodoanisole are solubilized in 750 ml of anhydrous DMF. 24.4 ml of triethylamine are added and the solution is then degassed under vacuum for 30 minutes. The reaction medium is placed under nitrogen, and then 6.3 g of tetrakis(triphenylphosphine)palladium(0) and 3.6 g of copper iodide are added. The mixture is stirred at AT under an argon atmosphere for 20 hours. The reaction crude is concentrated and purified by silica gel chromatography in dichloromethane. 48 g of the compound are recovered.

LC/MS (A): $MH^+$=402, tr=9.92 min

1c) 5-(4-methoxyphenyl-4-iodo-1-(4-tosylsulphonyl)-2,3-dihydro-1H-pyrrole-2-carboxylic acid ethyl ester 25.2 g of the compound obtained in the preceding stage 1b) are dissolved in 140 ml of anhydrous acetonitrile in the presence of 26 g of potassium carbonate at 0° C. 48 g of solid iodine are added, in several small fractions, with stirring, at this temperature of 0° C. The mixture is left to return to AT for 18 hours. The reaction is stopped with a solution of sodium thiosulphate until discoloration occurs, and the organic phase is extracted with ethyl acetate. After drying over magnesium sulphate, filtration and concentration, 30 g of the expected compound are obtained.

LC/MS (A): $MH^+$=528, tr=10.57 min.

1d) 4-(2,4-dichlorophenyl)-5-(4-methoxyphenyl)-1-tosylsulphonyl-2,3-dihydro-1H-pyrrole-2-carboxylic acid ethyl ester 57 g of the compound obtained in the preceding stage 1c) and 24.7 g of 2,4-dichlorophenylboronic acid are solubilized in a mixture of 500 ml of methanol and 1600 ml of toluene, in the presence of 180 ml of a sodium carbonate solution (2N). The reaction medium is degassed under argon for 30 minutes and then 17.5 g of tetrakis(triphenylphosphine)palladium(0) are added. The solution is heated at 70° C. for 6 hours under an inert atmosphere. After cooling, the crude is filtered through celite gel and then concentrated, and the organic phase is extracted with ethyl acetate. After drying over magnesium sulphate, filtration and concentration, the crude is taken up in methanol and the precipitate obtained is filtered off. 49 g of the expected compound are obtained in the form of a beige powder.

LC/MS (A): $MH^+$=546, tr=11.91 min

1e) 4-(2,4-dichlorophenyl)-5-(4-methoxyphenyl)-1H-pyrrole-2-carboxylic acid ethyl ester 48.6 g of the compound obtained in the preceding stage 1d) are solubilized in 500 ml of anhydrous N,N-dimethylformamide. 26.8 ml of DBU (1,8-diaza-bicyclo[5.4.0]undecene) are then added and the mixture is heated at 100° C. for 18 hours. After concentration, the crude is solubilized in ethyl acetate and the organic phase is washed excessively with a 10% solution of HCl and then with a saturated aqueous solution of $KHSO_4$ and then a saturated aqueous solution of NaCl. After drying over magnesium sulphate, filtration and concentration, the residue is triturated from isopropyl ether. The latter is filtered off, and 30.6 g of the expected compound are recovered.

LC/MS (A): $MH^+$=390, tr=11.46 min

1f) 4-(2,4-dichlorophenyl)-5-(4-methoxyphenyl)-1-methyl-1H-pyrrole-2-carboxylic acid ethyl ester 15 g of the compound obtained in the preceding stage 1e) are solubilized in 85 ml of anhydrous N,N-dimethylformamide. 26.6 g of $K_2CO_3$ and 12 ml of iodomethane are then added and the mixture is left to stir at AT for 4 hours and 30 minutes. After concentration, the crude is solubilized in ethyl acetate and the organic phase is washed with a 5% solution of KHSO$_4$. After drying over magnesium sulphate, filtration and concentration, 15.5 g of the expected product are obtained.

LC/MS (A): MH$^+$=404, tr=12.34 min

1g) 4-(2,4-dichlorophenyl)-5-(4-hydroxyphenyl)-1-methyl-1H-pyrrole-2-carboxylic acid ethyl ester 14.8 g of the compound obtained in the preceding stage 1f) are solubilized in 750 ml of anhydrous dichoromethane. The solution is placed at −50° C. and then 260 ml of BBr$_3$ are added dropwise. The temperature is left to come back up to −5° C. and the stirring is maintained for 4 hours. The reaction is stopped by adding cold methanol, followed by evaporation at AT and coevaporation with methanol. The reaction crude is concentrated and purified by silica gel chromatography in dichloromethane. 11.56 g of the expected compound are recovered.

$^1$H NMR, (200 MHz): δ (ppm): 1.29: t: 3H; 3.72: s: 3H; 4.25: q: 2H; 6.75: d: 2H; 6.97-7.08: m: 4H; 7.25: dd: 1H; 7.54: d: 1H; 9.70: bs: 1H.

Preparation 2:

4-(2,4-dichlorophenyl)-5-(4-(3-hydroxypropoxy) phenyl)-1-methyl-1H-pyrrole-2-carboxylic acid

2a) 4-(2,4-dichlorophenyl)-5-(4-(3-hydroxypropoxy) phenyl)-1-methyl-1H-pyrrole-2-carboxylic acid ethyl ester 0.70 g of the compound obtained in stage 1g) of preparation 1 is solubilized in 90 ml of anhydrous acetone, and then 0.50 g of K$_2$CO$_3$, followed by 0.37 g of 3-bromo-1-propanol. The mixture is brought to reflux for 20 hours. The crude is filtered and the filtrate is concentrated. The reaction crude is purified by silica gel chromatography in a cyclohexane/ethyl acetate gradient (9/1 to 6/4 in 45 min.). 0.70 g of the expected compound is obtained.

LC/MS (C): MH$^+$=448, tr=2.02 min

2b) 4-(2,4-dichlorophenyl)-5-(4-(3-hydroxypropoxy) phenyl)-1-methyl-1H-pyrrole-2-carboxylic acid 0.70 g of the ester obtained in the preceding stage 2a) is solubilized in 15 ml of methanol. 5 ml of H$_2$O and then 0.44 g of KOH are added and the mixture is brought to reflux for 4 hours. Once cooled, the medium is acidified with an aqueous solution of HCl (10%) and the product is then extracted with EtOAc. The organic phase is dried over MgSO$_4$ and then filtered and concentrated. The reaction crude is purified by silica gel chromatography in a dichloromethane/methanol gradient (100/0 to 96/4 in 20 min.). 0.54 g of the expected compound is obtained.

LC/MS (B): MH$^+$=420, tr=7.01 min $^1$H NMR, (200 MHz): δ (ppm): 1.84: qui: 2H; 3.54: t: 2H; 3.73: s: 3H; 4.01: t: 2H; 4.52: bs; 1H; 6.88-6.98: m: 3H; 7.03-7.14: m: 3H; 7.26: dd: 1H; 7.55: d: 1H; 12.36: bs: 1H.

EXAMPLES

Example 1

1-[4-(2,4-dichlorophenyl)-5-(4-(3-hydroxypropoxy) phenyl)-1-methyl-1H-pyrrole-2-carbonyl]-4-phenylpiperidine-4-carboxamide 0.30 g of the compound obtained in stage 2b) of preparation 2 is solubilized in 15 ml of DMF in the presence of 0.28 g (0.37 ml) of DIPEA. 0.34 g of 4-phenylpiperidine-4-carboxamide hydrochloride is then added, followed by the addition of 0.41 g of HBTU and 0.05 g of HOBt. The mixture is left stirring for 2 hours 30 minutes at AT. Once concentrated, the crude is chromatographed on silica gel in a dichloromethane/methanol gradient (99/1 to 93/7 in 40 min.). The orange-coloured residue obtained is subsequently crystallized from EtOAc, so as to obtain 0.37 g of a white product.

$^1$H NMR, (200 MHz): δ (ppm): 1.76-1.92: m: 4H; 2.52-2.60: m: 2H; 3.21-3.42: m: 2H; 3.47-3.59: m: 5H; 4.01-4.08: m, 2H; 4.11-4.25: m: 2H; 4.53: t: 1H; 6.52: s: 1H; 6.90: d: 2H; 7.05-7.13: m: 4H; 7.18-7.46: m: 7H; 7.54: d: 1H.

Example 2

1'-[5-(4-(3-aminopropoxy)phenyl)-4-(2,4-dichlorophenyl)-1-methyl-1H-pyrrole-2-carbonyl][1,4']bipiperidinyl-4'-carboxamide

2A) 4-(2,4-dichlorophenyl)-5-(4-hydroxyphenyl)-1-methyl-1H-pyrrole-2-carboxylic acid 8.9 g of the ester obtained in stage 1g) of preparation 1 are solubilized in 220 ml of MeOH. 55 ml of H$_2$O and then 7.7 g of KOH are added and the mixture is brought to reflux for 4 hours. Once cooled, the medium is acidified with an aqueous solution of HCl (10%), and the product is then extracted with EtOAc. The organic phase is dried over MgSO$_4$, and then filtered and concentrated. 9.85 g of the expected compound are obtained.

LC/MS (A): MH$^+$=362, tr=8.91 min

2B) 1'-[4-(2,4-dichlorophenyl)-5-(4-hydroxyphenyl)-1-methyl-1H-pyrrole-2-carbonyl]-[1,4']bipiperidinyl-4'-carboxamide 9.3 g of the carboxylic acid obtained in the preceding stage 2A) are solubilized in 500 ml of DMF in the presence of 10 g (13.5 ml) of DIPEA, and then 10.9 g of [1,4']bipiperidinyl-4'-carboxamide are added, followed by the addition of 14.6 g of HBTU and 1.7 g of HOBt. The mixture is left stirring for 18 hours at AT.

Once concentrated, the crude is chromatographed on silica gel in a dichloromethane/methanol gradient (100/0 to 90/10). The residue obtained is then precipitated from dichloromethane, so as to obtain 8.88 g of the expected product.

LC/MS (A): MH$^+$=555, tr=6.69 min

2C) (3-{4-[5-(4'-Carbamoyl-[1,4']bipiperidinyl-1'-carbonyl)-3-(2,4-dichlorophenyl)-1-methyl-1H-pyrrol-2-yl]-phenoxy}propyl)carbamic acid tert-butyl ester 0.44 g of the compound obtained in the preceding stage 2B), 0.24 g of 3-bromopropylcarbamic acid tert-butyl ester, 0.39 g of $CsCO_3$ and also 0.03 g of NaI are suspended in 13 ml of acetonitrile. The mixture is stirred under an inert atmosphere at 70° C. for 16 hours. The crude is filtered and the filtrate is concentrated. The reaction crude is purified by silica gel chromatography in a dichloromethane/methanol gradient (100/0 to 98/2 in 20 min.). 0.50 g of the expected compound is obtained.

LC/MS (A): $MH^+$=712, tr=7.95 min

2D) 1'-[5-(4-(3-aminopropoxy)phenyl)-4-(2,4-dichlorophenyl)-1-methyl-1H-pyrrole-2-carbonyl][1,4']bipiperidinyl-4'-carboxamide 0.48 g of the compound obtained in the preceding stage 2C) is solubilized in 3 ml of dichloromethane, and then 0.77 g (0.5 ml) of TFA is added. The mixture is left to stir at AT for 18 hours. The crude is concentrated and coevaporated with dichloromethane. The reaction crude is purified by silica gel chromatography in a dichloromethane/methanol gradient (100/0 to 80/20). The residue is then taken up in the minimum amount of dichloromethane and then hydrochloric ether is added. The medium is then diluted with ethyl ether and left to stir for 1 hour at AT. After filtration and washes with ethyl ether, 0.40 g of the expected compound is obtained.

$^1$H NMR, (200 MHz): δ (ppm): 1.22-1.41: m: 4H; 1.52-2.18: m: 8H; 2.61-2.93: m: 6H; 3.41-3.51: m: 5H; 4.00: t: 2H; 4.36-4.49: m: 2H; 6.51: s: 1H; 6.88: d: 2H; 7.05-7.13: m: 4H; 7.05-7.10: m: 3H; 7.26: dd: 1H; 7.51: d: 1H; 7.87-7.95: bs: 3H; 8.15-8.30: 2 bs: 2H.

Example 3

1'-[4-(2,4-dichlorophenyl)-5-(4-(3-methanesulphonylamino-propoxy)phenyl)-1-methyl-1H-pyrrole-2-carbonyl][1,4']bipiperidinyl-4'-carboxamide 0.39 g of the compound obtained in stage 2D) of Example 2 is solubilized in 4 ml of DCM, 0.129 g (0.18 ml) of triethylamine and then, slowly, 0.08 g of methanesulphonyl chloride. The mixture is left to stir at AT for 20 hours. After concentration, the crude is solubilized in ethyl acetate and the organic phase is washed successively with a 10% solution of HCl and with a saturated aqueous solution of NaCl. After drying over magnesium sulphate, filtration and concentration, the residue is purified by silica gel chromatography in a dichloromethane/methanol gradient (100/0 to 95/5). The latter is filtered, and 0.32 g of the expected compound is recovered.

$^1$H NMR, (200 MHz): δ (ppm): 1.28-1.54: m: 6H; 1.66-1.99: m: 6H; 2.39-2.50: m: 2H; 2.89: s: 3H; 3.03-3.15: m: 2H; 3.37-3.53: m: 5H; 3.84-4.05: m: 4H; 6.50: s: 1H; 6.90: d: 2H; 7.02-7.14: m: 6H; 7.26: dd: 1H; 7.54: d: 1H.

Example 4

1'-[5-(4-Carbamoylmethoxyphenyl)-4-(2,4-dichlorophenyl)-1-methyl-1H-pyrrole-2-carbonyl][1,4']bipiperidinyl-4'-carboxamide

4A) {4-[5-(4'-Carbamoyl-[1,4']bipiperidinyl-1'-carbonyl)-3-(2,4-dichlorophenyl)-1-methyl-1H-pyrrol-2-yl]phenoxy}acetic acid tert-butyl ester 0.60 g of the compound obtained in stage 2B) of Example 2 are solubilized in 20 ml of DMF and then 0.22 g of $K_2CO_3$ followed by 0.42 g of tert-butyl bromoacetate. The mixture is brought to reflux for 19 hours. The crude is filtered and the filtrate is concentrated. The reaction crude is purified by silica gel chromatography in a cyclohexane/ethyl acetate gradient (20/80 to 0/100 in 20 min.). 0.72 g of the expected compound is obtained.

LC/MS (A): $MH^+$=669, tr=8.01 min

4B) {4-[5-(4'-Carbamoyl-[1,4']bipiperidinyl-1'-carbonyl)-3-(2,4-dichlorophenyl)-1-methyl-1H-pyrrol-2-yl]phenoxy}acetic acid 0.72 g of the compound obtained in the preceding stage 4A) is solubilized in 15 ml of dichloromethane, and then 8 g (5.4 ml) of TFA are added. The reaction medium is left to stir at AT for 6 hours. The mixture is concentrated and coevaporated with dichloromethane. The crude is taken up in ethyl acetate and the organic phase is then washed successively with a saturated solution of $NaHCO_3$, with a 5% solution of $KHSO_4/K_2SO_4$ and then with a saturated solution of NaCl. After drying over magnesium sulphate, filtration and concentration, 0.46 g of the expected compound is obtained.

LC/MS (A): $MH^+$=613, tr=6.73 min

4C) 1'-[5-(4-Carbamoylmethoxyphenyl)-4-(2,4-dichlorophenyl)-1-methyl-1H-pyrrole-2-carbonyl][1,4']bipiperidinyl-4'-carboxamide 0.46 g of the compound of the preceding stage 4B) is solubilized in 15 ml of DMF, and 0.13 g of carbonyl diimidazole is added. The stirring is maintained for 1 hour under a nitrogen atmosphere, and then ammonia is bubbled in for 30 min. The mixture is then stoppered and left to stir at AT for 48 hours. After concentration, the crude is solubilized in dichloromethane, and the organic phase is washed with a saturated aqueous solution of NaCl. After drying over magnesium sulphate, filtration and concentration, the residue is purified by silica gel chromatography in a dichloromethane/ammoniacal methanol gradient (100/0 to 96/4). 0.39 g of the expected compound is obtained.

$^1$H NMR, (250 MHz): δ (ppm): 1.23-1.50: m: 6H; 1.51-1.91: m: 4H; 2.34-2.42: m: 2H; 3.31-3.49: m: 5H; 3.79-3.81: m, 2H; 4.38: s: 2H; 6.48: s: 1H; 6.89: d: 2H; 6.99-7.11: m: 5H; 7.21: dd: 1H; 7.37: bs: 1H; 7.50: d: 1H.

Example 5

1'-[4-(2,4-dichlorophenyl)-5-(4-(3-methylaminopropoxy)phenyl)-1-methyl-1H-pyrrole-2-carbonyl][1,4']bipiperidinyl-4'-carboxamide

5A) 1'-[5-(4-(3-chloropropoxy)phenyl)-4-(2,4-dichlorophenyl)-1-methyl-1H-pyrrole-2-carbonyl][1,4']bipiperidinyl-4'-carboxamide 1 g of the compound obtained in stage 2B) of Example 2 is solubilized in 30 ml of anhydrous DMF, and then 0.75 g of $K_2CO_3$ followed by 0.85 g (0.53 ml) of 1-bromo-3-chloropropane are added. The mixture is brought to reflux for 20 hours. The crude is filtered and the filtrate is concentrated.

The reaction crude is purified by a silica gel chromatography in a dichloromethane/methanol gradient (100/0 to 95/5). 1.1 g of the expected compound are obtained.

LC/MS (A): MH⁺=633, tr=8.10 min 5B) 1'-[4-(2,4-dichlorophenyl)-5-(4-(3-iodopropoxy) phenyl)-1-methyl-1H-pyrrole-2-carbonyl][1,4']bipiperidinyl-4'-carboxamide 1.1 g of the compound of the preceding stage 5A) are solubilized in 12 ml of acetonitrile and then 1.9 g of NaI are added. The mixture is left to stir at 75° C. for 18 hours. After concentration, the crude is solubilized in dichloromethane and the organic phase is washed with a saturated aqueous solution of NaCl. After drying over magnesium sulphate, filtration and concentration, 1.16 g of the expected compound are obtained.

LC/MS (A): MH⁺=723, tr=8.42 min 5C) 1'-[4-(2,4-dichlorophenyl)-5-(4-(3-methylaminopropoxy)phenyl)-1-methyl-1H-pyrrole-2-carbonyl] [1,4']bipiperidinyl-4'-carboxamide 0.20 g of the compound obtained in the preceding stage 5B) is solubilized in 10 ml of methylamine (as a 2M solution in THF), and then the solution is left stoppered and stirring at 105° C. for 20 hours. After concentration, the crude is solubilized in dichloromethane and the organic phase is washed with a saturated aqueous solution of NaCl. After drying over magnesium sulphate, filtration and concentration, the residue is purified by silica gel chromatography in a dichloromethane/ammoniacal methanol gradient (95/5 to 70/30). 0.25 g of the expected compound is obtained.

$^1$H NMR, (200 MHz): δ (ppm): 1.34-1.55: m: 6H; 1.68-1.97: m: 6H; 2.26: s: 3H; 2.41-2.48: m: 4H; 2.57: t, 2H; 3.37-3.53: m: 5H; 3.84-4.04: m: 4H; 6.49: s: 1H; 6.89: d: 2H; 7.02-7.13: m: 5H; 7.26: dd: 1H; 7.54: d: 1H.

Example 6

1-[4-(2,4-dichlorophenyl)-5-[4-(3-hydroxypropoxy) phenyl]-1-methyl-1H-pyrrole-2-carbonyl]-4-(3-fluorobenzylamino)piperidine-4-carboxamide This compound is prepared according to a procedure similar to that of Example 1, starting from 0.18 g of the compound obtained in stage 2B) of preparation 2. The reactant used in this case is 4-(3-fluorobenzylamino)piperidine-4-carboxamide dihydrochloride.

The purification is carried out by silica gel chromatography in a dichloromethane/methanol gradient (99/1 to 95/5 in 40 min.). 0.11 g of the expected product is obtained.

$^1$H NMR, (250 MHz): δ (ppm): 1.68-1.95: m: 6H; 2.56-2.60: m: 1H; 3.52-3.68: m: 6H; 3.54: s: 3H; 3.89-3.97: m: 2H; 4.03: t: 2H; 4.54: t: 1H; 6.51: s: 1H; 6.92: d: 2H; 7.03-7.14: m: 5H; 7.21-7.28: m: 3H; 7.33-7.41 m: 2H; 7.56: s: 1H.

Example 7

1-[5-(4-carbamoylmethoxy)phenyl-4-(2,4-dichlorophenyl)-1-methyl-1H-pyrrole-2-carbonyl]-4-phenylpiperidine-4-carboxamide 7A) 1'-[4-(2,4-dichlorophenyl)-5-(4-hydroxyphenyl)-1-methyl-1H-pyrrole-2-carbonyl]-4-phenylpiperidine-4-carboxamide The compound is prepared according to a procedure similar to that of stage 2B) of Example 2, starting from 0.4 g of the compound obtained in stage 2A). The reactant used is 4-phenylpiperidine-4-carboxamide hydrochloride.

The purification is carried out by silica gel chromatography in a dichloromethane/ammoniacal methanol gradient (100/0 to 90/10). 0.26 g of the expected product is obtained.

$^1$H NMR, (200 MHz): δ (ppm): 1.74-1.82: m: 2H; 2.50-2.60: m: 2H; 3.18-3.37: m: 2H; 3.45: s: 3H; 4.12-4.27: m: 2H; 6.51: s: 1H; 6.71: d: 2H; 6.94-7.12: m: 4H; 7.18-7.47: m: 7H; 7.53: d: 1H; 9.8: bs: 1H.

7B) 1-[5-(4-carbamoylmethoxy)phenyl-4-(2,4-dichlorophenyl)-1-methyl-1H-pyrrole-2-carbonyl]-4-phenylpiperidine-4-carboxamide 0.25 g of the compound obtained in the preceding stage 7A), 0.065 g of 2-chloroacetamide, 0.13 g of K₂CO₃ and also 0.03 g of NaI are suspended in 9 ml of acetone. The mixture is stirred under an inert atmosphere at 50° C. for 10 hours. After the addition of 0.043 g of 2-chloroacetamide, the reaction medium is left to stir at 50° C. for 60 hours. Next, 0.043 g of 2-chloroacetamide is added to the reaction medium.

After filtration and concentration, the reaction crude is purified by silica gel chromatography in an isocratic mixture of heptane/EtOAc/ammoniacal methanol (40/60/10). 0.15 g of the expected product is obtained.

$^1$H NMR, (250 MHz): δ (ppm): 1.79-1.89: m: 2H; 2.50-2.57: m: 2H; 3.28-3.30: m: 2H; 3.52: s: 3H; 4.16-4.22: m, 2H; 4.43: s: 2H; 6.53: s: 1H; 6.94: d: 2H; 7.09-7.15: m: 4H; 7.22-7.28: m: 3H; 7.33-7.44: m: 5H; 7.52-7.56: m: 2H.

Example 8

1-[4-(2-chlorophenyl)-5-[4-(3-hydroxypropoxy)phenyl]-1-methyl-1H-pyrrole-2-carbonyl]-4-(4-fluorobenzylamino)piperidine-4-carboxamide The compound is prepared according to a procedure identical to that of Example 1, starting from 0.30 g of the compound obtained in stage 2B) of preparation 2. The reactant used in this case is 4-(4-fluorobenzylamino)piperidine-4-carboxamide dihydrochloride.

The purification is carried out by silica gel chromatography in a dichloromethane/methanol gradient (99/1 to 96/4 in 20 min.). 0.27 g of the expected product is obtained.

$^1$H NMR, (250 MHz): δ (ppm): 1.64-1.94: m: 6H; 2.49-2.50: m: 1H; 3.49-3.70: m: 6H; 3.52: s: 3H; 3.90-4.05: m: 4H; 4.55: t: 1H; 6.49: s: 1H; 6.90: d: 2H; 7.06-7.24: m: 8H; 7.39-7.48: m: 4H.

Tables 1 and 2 indicate the chemical structures of some compounds according to the invention and also the physical properties thereof (analysis by LC/UV/MS coupling: liquid chromatography/UV detection/mass spectrometry). The compounds listed are prepared according to the preparation processes described above, and in particular according to procedures similar to those described in Examples 1 to 8.

TABLE 1
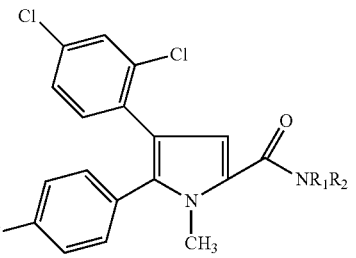
| Compounds | —Y—A—R$_9$ | —CONR$_1$R$_2$ | Mp | LC/MS MH$^+$; tr; (conditions) |
|---|---|---|---|---|
| 1 (Ex 2) | —O—(CH$_2$)$_3$—NH$_2$ | 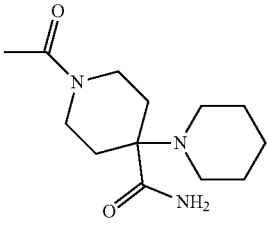 [SMILES: CC(=O)N1CCC(C(N)=O)(N2CCCCC2)CC1] | 245° C. | MH$^+$ = 612<br>tr = 5.71<br>(A) |
| 2 | —O—(CH$_2$)$_3$—CONH$_2$ | 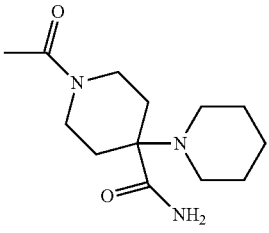 [SMILES: CC(=O)N1CCC(C(N)=O)(N2CCCCC2)CC1] | 163° C. | MH$^+$ = 604<br>tr = 6.69<br>(A) |
| 3 (Ex 3) | —O—(CH$_2$)$_3$—NHSO$_2$CH$_3$ | 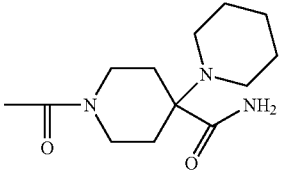 [SMILES: CC(=O)N1CCC(C(N)=O)(N2CCCCC2)CC1] | 209 C. | MH$^+$ = 690<br>tr = 7.08<br>(A) |
| 4 (Ex 4) | —O—CH$_2$—CONH$_2$ | 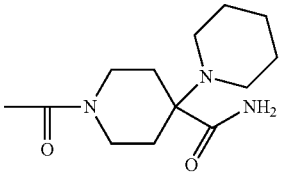 [SMILES: CC(=O)N1CCC(C(N)=O)(N2CCCCC2)CC1] | 225° C. | MH$^+$ = 612<br>tr = 6.50<br>(A) |
| 5 | —O—(CH$_2$)$_3$—NHCOCH$_2$OH | 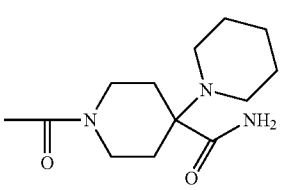 [SMILES: CC(=O)N1CCC(C(N)=O)(N2CCCCC2)CC1] | | MH$^+$ = 670<br>tr = 6.63<br>(A) |
| 6 | —O—(CH$_2$)$_3$—OH |  | 136° C. | MH$^+$ = 613<br>tr = 22.3<br>(B) |

TABLE 1-continued

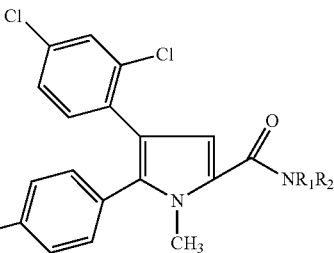

| Compounds | —Y—A—R$_9$ | —CONR$_1$R$_2$ | Mp | LC/MS MH$^+$; tr; (conditions) |
|---|---|---|---|---|
| 7 | —O—(CH$_2$)$_3$—NSO$_2$CH$_3$ | (4,4-difluoropiperidin-1-yl)-1-acetylpiperidine-4-carboxamide | 224 C. | MH$^+$ = 726 tr = 9.38 (A) |
| 8 (Ex 5) | —O—(CH$_2$)$_3$—NHCH$_3$ | (piperidin-1-yl)-1-acetylpiperidine-4-carboxamide | 186° C. | MH$^+$ = 626 tr = 5.78 (A) |
| 9 | methoxypropyl-pyrrolidine | (piperidin-1-yl)-1-acetylpiperidine-4-carboxamide | 233° C. | MH$^+$ = 666 tr = 5.94 (A) |
| 10 (Ex 1) | —O—(CH$_2$)$_3$—OH | 4-phenyl-1-acetylpiperidine-4-carboxamide | 121° C. | MH$^+$ = 605 tr = 2.86 (C) |
| 11 (Ex 6) | —O—(CH$_2$)$_3$—OH | 4-[(3-fluorobenzyl)amino]-1-acetylpiperidine-4-carboxamide | | MH$^+$ = 653 tr = 2.34 (C) |
| 12 | —O—(CH$_2$)$_2$—OH | 4-phenyl-1-acetylpiperidine-4-carboxamide | 205° C. | |

TABLE 1-continued
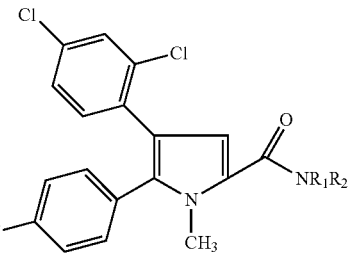
| Compounds | —Y—A—R$_9$ | —CONR$_1$R$_2$ | Mp | LC/MS MH$^+$; tr; (conditions) |
|---|---|---|---|---|
| 13 | —O—(CH$_2$)$_2$—OH | 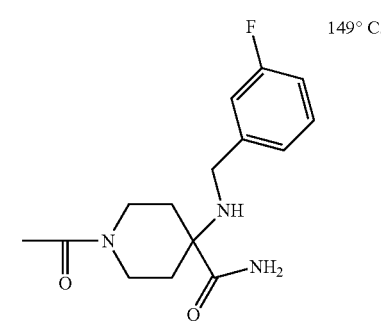 | 149° C. | |
| 14 | —O—(CH$_2$)$_3$—CONH$_2$ | 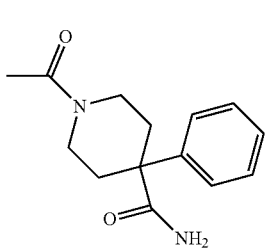 [SMILES: CC(=O)N1CCC(C(N)=O)(c2ccccc2)CC1] | 130° C. | MH$^+$ = 680 Tr = 8.84 (B) |
| 15 | —O—(CH$_2$)$_3$—CONH$_2$ | | 143° C. | MH$^+$ = 633 tr = 1.50 (C) |

TABLE 1-continued
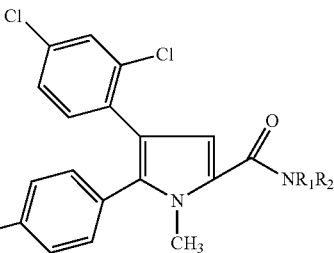
| Compounds | —Y—A—R₉ | —CONR₁R₂ | Mp | LC/MS MH⁺; tr; (conditions) |
|---|---|---|---|---|
| 16 (Ex 7) | —O—CH₂—CONH₂ | 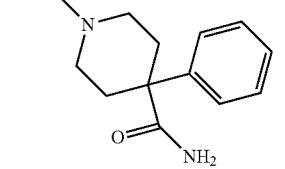 | 141° C. | MH⁺ = 605 tr = 2.53 (D) |
| 17 | —O—CH₂—CONH₂ | 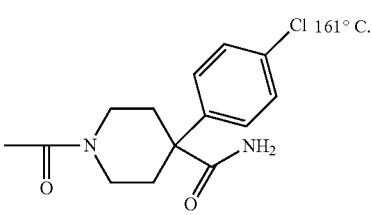 | | MH⁺ = 652 tr = 1.16 (C) |
| 18 | —O—(CH₂)₂—OH | 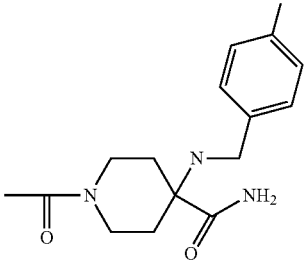 | 161° C. | MH⁺ = 626 tr = 2.96 (D) |
| 19 | —O—(CH₂)₂—OH | | 149° C. | MH⁺ = 639 tr = 8.99 (B) |

TABLE 2
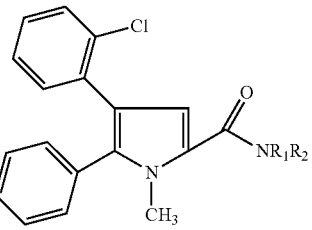
| Compounds | —Y—A—R$_9$ | —CONR$_1$R$_2$ | Mp | LC/MS MH$^+$; tr; (conditions) |
|---|---|---|---|---|
| 20 | —O—(CH$_2$)$_2$—OH | 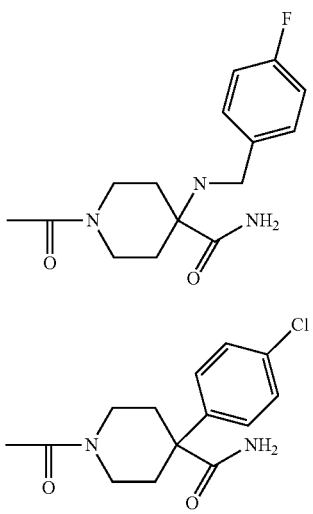 | 195° C. | MH$^+$ = 605<br>tr = 1.91<br>(D) |
| 21 | —O—(CH$_2$)$_2$—OH | 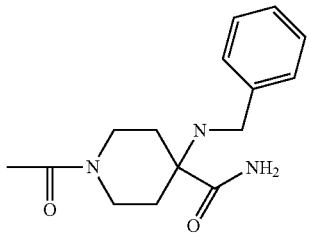 [SMILES: CC(=O)N1CCC(NCc2ccccc2)(C(N)=O)CC1] | 188° C. | MH$^+$ = 592<br>tr = 2.65<br>(D) |
| 22 | —O—(CH$_2$)$_2$—OH | | 169° C. | MH$^+$ = 587<br>tr = 1.85<br>(D) |
| 23 | —O—(CH$_2$)$_2$—OH | 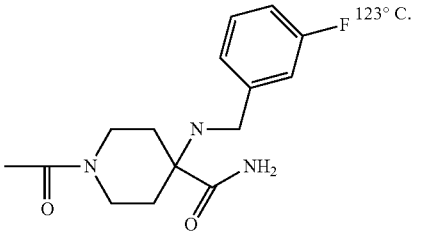 | 123° C. | MH$^+$ = 605<br>tr = 1.93<br>(D) |
| 24 | —O—(CH$_2$)$_3$—OH | 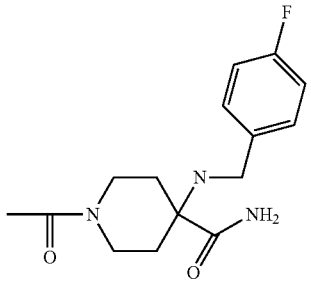 [SMILES: CC(=O)N1CCC(NCc2ccc(F)cc2)(C(N)=O)CC1] | 220° C. | MH$^+$ = 619<br>tr = 2.03<br>(D) |

TABLE 2-continued

| Compounds | —Y—A—R₉ | —CONR₁R₂ | Mp | LC/MS MH⁺; tr; (conditions) |
|---|---|---|---|---|
| 25 (Ex 8) | —O—(CH₂)₃—OH | | 171° C. | MH⁺ = 601 tr = 1.99 (D) |
| 26 | —O—(CH₂)₃—OH | | 176° C. | MH⁺ = 606 tr = 2.77 (D) |
| 27 | —O—(CH₂)₃—OH | | 237° C. | MH⁺ = 619 tr = 2.04 (D) |

TABLE 2-continued

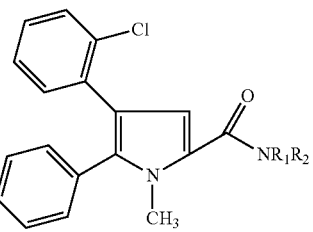

| Compounds | —Y—A—R$_9$ | —CONR$_1$R$_2$ | Mp | LC/MS MH$^+$ tr; (conditions) |
|---|---|---|---|---|
| 28 | —O—(CH$_2$)$_3$—OH | (structure) | 190° C. | MH$^+$ = 618<br>tr = 1.78<br>(D) |
| 29 | —O—(CH$_2$)$_3$—OH | (structure) | 175° C. | MH$^+$ = 618<br>tr = 1.80<br>(D) |

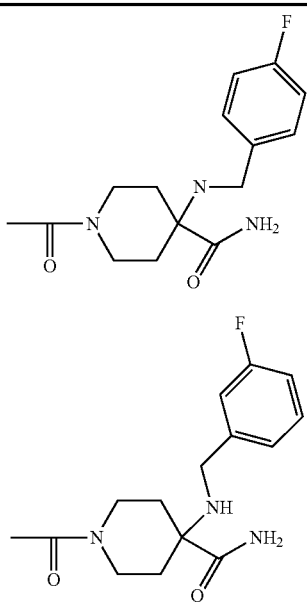

The compounds of Formula (I) have a very good in vitro affinity (IC$_{50}$≦5×10$^{-7}$M) for cannabinoid CB$_1$ receptors, under the experimental conditions described by M. Rinaldi-Carmona et al. (FEBS Letters, 1994, 350, 240-244).

The antagonist nature of the compounds of Formula (I) was determined, in vitro, by the results obtained in adenylate cyclase inhibition models as described in M. Bouaboula et al., J. Biol. Chem., 1995, 270, 13973-13980, M. Rinaldi-Carmona et al., J. Pharmacol. Exp. Ther., 1996, 278, 871-878 and M. Bouaboula et al., J. Biol. Chem., 1997, 272, 22330-22339.

The weak penetration of the compounds of Formula (I) across the blood-brain barrier (BBB) was evaluated in vivo by:

Measurement (1): quantification of the compounds of Formula (I) (unchanged) in samples of mouse brain after intravenous or oral administration, by means of an analytical technique (LC-MS/MS).

The ratio $\frac{\text{amount present in the brain}}{\text{amount present in the plasma}}$ of less than 0.2 reflects a weak penetration of the compound into of the brain.

Measurement (2): measurement of the interaction of the compounds of Formula (I) with the CB1 receptors present in the brain in mice by means of a test for ex vivo binding of [3H]-CP55940 (CB1 agonist) after intravenous administration (10 mg/kg) as described in M. Rinaldi-Carmona et al., FEBS Letters, 1994, 350, 240-244 and M. Rinaldi-Carmona et al., Life Sciences, 1995, 56, 1941-1947, M. Rinaldi-Carmona et al., J. Pharmacol. Exp. Ther., 2004, 310, 905-914.

A percentage inhibition of [3H]-CP55940 binding in the brain of less than 50% at 10 mg/kg reflects a weak penetration into the brain. Preferably, this percentage is less than 40%, and more preferably less than 30%.

Measurement (3): measurement of the blocking, by the compounds of Formula (I), of the hypothermic effect induced by a CB1 receptor agonist (CP55940), after intravenous administration, as described in Rinaldi-Carmona M. et al., JPET 2004, 310, 905-914).

A percentage reversion of the effect of CP55940 of less than 50% at 10 mg/kg reflects a weak penetration into the brain. Preferably, this percentage is less than 40%, and more preferably less than 30%.

The interaction of the compounds of Formula (I) according to the invention with the CB1 receptors present at the periphery was demonstrated in mice by measuring the blocking of the inhibitory effect induced by a CB1 receptor agonist (CP55940) on gastrointestinal transit, after oral administration, as described in M. Rinaldi-Carmona et al., J. Pharmacol. Exp. Ther., 2004, 310, 905-914. A percentage reversion of the effect of CP55940 of greater than 50% at 10 mg/kg reflects a significant antagonist capacity at the level of the CB1 receptors present in the periphery. Preferably, the percentage reversion is between 70% and 100%.

By way of examples, the following measurements were carried out for compounds No. 11, 16 and 24 of Tables 1 and 2, and rimonabant as control compound.

|  | Ratio: Amount present in the brain/ Amount present in the plasma [iv at 3 mg/kg, according to measurement (1)] | % inhibition of [3H]-CP55940 binding at the level of the brain, iv at 10 mg/kg [CB1 receptors present in the brain, according to measurement (2)]. | % reversion of the hypothermic effect of CP55940, iv at 10 mg/kg [CB1 receptors present in the brain, according to measurement (3)]. | % reversion of the effect of CP55940 on GI transit, per os at 10 mg/kg [CB1 receptors present at the periphery]. |
|---|---|---|---|---|
| Control: rimonabant | 1.8 | 100% | 100% | 100% |
| Compound No. 11 | / | 25% | 64% | / |
| Compound No. 16 | 0.05 | 8% | 3% | 76% |
| Compound No. 24 | / | 1% | 20% | 100% |

The compounds of Formula (I) are compatible with use thereof as a medicament.

Thus, according to another of its aspects, a subject of the invention is medicaments for human or veterinary medicine, which comprise a compound of Formula (I), or an addition salt of the latter with a pharmaceutically acceptable acid Thus, the compounds according to the invention can be used in humans or in animals (in particular in mammals, including, in a non-limiting manner, dogs, cats, horses, cattle, sheep) in the treatment or prevention of diseases involving cannabinoid $CB_1$ receptors.

For example, and in a non-limiting manner, the compounds of Formula (I) are of use as psychotropic medicaments, in particular for the treatment of psychiatric disorders including anxiety, depression, mood disorders, insomnia, delirious conditions, obsessive disorders, psychoses in general, schizophrenia, attention deficit hyperactivity disorders (ADHD) in hyperkinetic children, and also for the treatment of disorders related to the use of psychotropic substances, in particular in the case of a substance abuse and/or a substance dependence, including alcohol dependence and nicotine dependence.

The compounds of Formula (I) according to the invention can be used as medicaments for the treatment of migraine, stress, diseases of psychosomatic origin, panic attacks, epilepsy, motor disorders, in particular dyskinesia or Parkinson's disease, shaking and dystonia.

The compounds of Formula (I) according to the invention can also be used as medicaments in the treatment of memory disorders, cognitive disorders, in particular in the treatment of senile dementia and Alzheimer's disease, and also in the treatment of attention or consciousness disorders.

Furthermore, the compounds of Formula (I) may be of use as neuroprotective agents, in the treatment of ischemia and cranial trauma and the treatment of acute or chronic neurodegenerative diseases, including chorea, Huntington's chorea and Tourette's syndrome.

The compounds of Formula (I) according to the invention can be used as medicaments in the treatment of pain: neuropathic pain, acute peripheral pain, chronic pain of inflammatory origin, pain induced by an anticancer treatment.

The compounds of Formula (I) according to the invention can be used as medicaments in human or veterinary medicine, in the prevention and treatment of metabolic disorders, appetite disorders, appetence disorders (appetence for sugars, carbohydrates, drugs, alcohol or any appetizing substance) and/or eating behaviour disorders, in particular for the treatment of obesity or bulimia and also for the treatment of type II diabetes or non-insulin-dependent diabetes and for the treatment of dyslipidaemia and metabolic syndrome. Thus, the compounds of Formula (I) according to the invention are of use in the treatment of obesity and the risks associated with obesity, in particular the cardiovascular risks.

Furthermore, the compounds of Formula (I) according to the invention can be used as medicaments in the treatment and prevention of gastrointestinal disorders, diarrhoea disorders, ulcers, vomiting, bladder and urinal disorders, liver diseases which may or may not be of alcoholic origin, such as chronic cirrhosis, fibrosis, hepatic steatosis or steatohepatitis; and also disorders of endocrine origin, cardiovascular disorders, hypotension, atherosclerosis, hemorrhagic shock, septic shock, asthma, chronic bronchitis, chronic obstructive pulmonary disorders, Raynaud's syndrome, glaucoma, fertility disorders, premature birth, interruption of pregnancy, inflammatory phenomena, immune system diseases, in particular autoimmune and neuroinflammatory diseases such as rheumatoid arthritis, reaction arthritis, diseases resulting in demyelination, multiple sclerosis, infectious and viral diseases such as encephalitis, cerebral strokes, and also as medicaments for anticancer chemotherapy, for the treatment of Guillain-Barré syndrome and for the treatment of bone diseases and osteoporosis.

Furthermore, the compounds of Formula (I) according to the invention can be used for their protective effects against drug-induced cardiotoxicity.

According to the present invention, the compounds of Formula (I) are most particularly of use for the preparation of medicaments of use in the prevention and treatment of psychiatric disorders, in particular schizophrenia, attention and consciousness disorders, attention deficit hyperactivity disorders (ADHD) in hyperkinetic children; in the prevention and treatment of memory deficiencies and cognitive disorders; of dependence on and withdrawal from a substance, in particular alcohol dependence, nicotine dependence, alcohol withdrawal and tobacco withdrawal; acute or chronic neurodegenerative diseases.

According to the present invention, the compounds of the Formula (I) are also most particularly of use for the preparation of medicaments of use in the treatment and prevention of appetite disorders, appetence disorders, metabolic disorders, obesity, type II diabetes, metabolic syndrome, dyslipidaemia, gastrointestinal disorders, inflammatory phenomena, immune system diseases, psychotic disorders, alcohol dependence and nicotine dependence.

According to one of its aspects, the present invention relates to the use of a compound of Formula (I), or a pharmaceutically acceptable salt thereof, for the treatment of the disorders and diseases indicated above.

According to another of its aspects, the present invention relates to pharmaceutical compositions comprising, as active ingredient, a compound according to the invention. These pharmaceutical compositions contain an effective dose of at least one compound according to the invention, or a pharmaceutically acceptable salt of said compound, and also at least one pharmaceutically acceptable excipient.

Said excipients are selected, according to the pharmaceutical form and the method of administration desired, from the usual excipients which are known to those skilled in the art.

The pharmaceutical compositions according to the present invention may contain, along with a compound of Formula (I), one (or more) other active ingredient(s) that is (are) of use in the treatment of the disorders and diseases indicated above.

Thus, a subject of the present invention is also pharmaceutical compositions containing a compound of Formula (I) according to the present invention combined with one (or more) active ingredient(s) selected from one of the following therapeutic classes:
  another cannabinoid $CB_1$ receptor antagonist or allosteric modulators of cannabinoid $CB_1$ receptors;
  a cannabinoid $CB_2$ receptor modulator;
  an angiotensin II $AT_1$ receptor antagonist;
  a converting enzyme inhibitor;
  a calcium antagonist;
  a diuretic;
  a beta-blocker;
  an antihyperlipemic or an antihypercholesterolemic;
  an antidiabetic agent;
  another anti-obesity agent or agent acting on metabolic disorders;
  a nicotine agonist, a partial nicotine agonist;
  an antidepressant, an antipsychotic, an anxiolytic;
  an anticancer agent or an antiproliferative agent;
  an opioid antagonist;
and also:
  an agent for improving memory;
  an agent that can be used in the treatment of alcoholism or withdrawal symptoms;
  an agent that can be used for treating osteoporosis;
  a non-steroidal or steroidal anti-inflammatory;
  an anti-infective;
  an analgesic;
  an antiasthmatic.

The expression "angiotensin II $AT_1$ receptor antagonist" is intended to mean a compound such as candesartan cilexitil, eprosartan, irbesartan, losartan potassium, olmesartan medoxomil, telmisartan or valsartan, it being possible for each of these compounds to itself be combined with a diuretic such as hydrochlorothiazide.

The term "converting enzyme inhibitor" is intended to mean a compound such as alacepril, benazepril, captopril, cilazapril, enalapril, enalaprilat, fosinopril, imidapril, lisinopril, moexipril, perindopril, quinapril, ramipril, spirapril, temocapril, trandolapril or zofenopril, it being possible for each of these compounds itself to be combined with a diuretic such as hydrochlorothiazide or indapamide or with a calcium antagonist such as amlodipine, diltiazem, felodipine or verapamil.

The term "calcium antagonist" is intended to mean a compound such as amlodipine, aranidipine, benidipine, bepridil, cilnidipine, diltiazem, efonidipine hydrochloride ethanol, fasudil, felodipine, isradipine, lacidipine, lercanidipine hydrochloride, manidipine, mibefradil hydrochloride, nicardipine, nifedipine, nilvadipine, nimodipine, nisoldipine, nitrendipine, terodiline or verapamil.

The term "beta-blocker" is intended to mean a compound such as acebutolol, alprenolol, amosulalol, arotinolol, atenolol, befunolol, betaxolol, bevantolol, bisoprolol, bopindolol, bucumolol, bufetolol, bunitrolol, butofilolol, carazolol, carteolol, carvedilol, cloranolol, epanolol, esmolol, indenolol, labetalol, landiolol, levobunolol, levomoprolol, mepindolol, metipranolol, metoprolol, nadolol, nebivolol, nifenalol, nipradilol, oxprenolol, penbutolol, pindolol, propranolol, salmeterol, sotalol, talinolol, tertatolol, tilisolol, timolol, xamoterol or xibenolol.

The term "antihyperlipemic" or "antihypercholesterolemic" is intended to mean a compound selected from fibrates, such as alufibrate, beclobrate, bezafibrate, ciprofibrate, clinofibrate, clofibrate, etofibrate or fenofibrate; statins (inhibitors of HMG-CoA reductase), such as atorvastatin, fluvastatin sodium, lovastatin, pravastatin, rosuvastatin, simvastatin, or a compound such as acipimox, aluminium nicotinate, azacosterol, cholestyramine, dextrothyroxine, meglutol, niceritrol, nicoclonate, nicotinic acid, beta-sitosterol or tiadenol.

The term "antidiabetic agent" is intended to mean a compound belonging to one of the following classes: sulphonylureas, biguanidines, alpha-glucosidase inhibitors, thiazolidinediones, metiglinides, such as acarbose, acetohexamide, carbutamide, chlorpropamide, glibenclamide, glibornuride, gliclazide, glimepiride, glipizide, gliquidone, glisoxepide, glybuzole, glymidine, metahexamide, metformin, miglitol, nateglinide, pioglitazone, repaglinide, rosiglitazone, tolazamide, tolbutamide, troglitazone or voglibose, and also insulin and insulin analogues.

The expression "other anti-obesity agent or agent for acting on metabolic disorders" is intended to mean a compound such as amfepramone, benfluorex, benzphetamine, indanorex, mazindole, mefenorex, methamphetamine, D-norpseudoephedrine, sibutramine, a topiramate, a lipase inhibitor (orlistat cetilistat), a PPAR agonist (Peroxisome Proliferator Activated Receptor Agonist), a dopamine agonist, a leptin receptor agonist, a serotonin re-uptake inhibitor, a beta-3 agonist, a CCK-A agonist, an NPY inhibitor, an MC4 (melanocortin 4) receptor agonist, an MCH (Melanin Concentrating Hormone) receptor antagonist, an orexin antagonist, a phosphodiesterase inhibitor, an 11 HSD (11-hydroxy steroid dehydrogenase inhibitor), a DPP-IV (dipeptidyl peptidase IV) inhibitor, a histamine H3 antagonist (or inverse agonist), a CNTF (Ciliary Neurotrophic Factor) derivative, a GHS (Growth Hormone Secretagogue) receptor agonist, a ghrelin modulator, a diacyglycerol acyltransferase (DGAT) inhibitor, a phosphodiesterase (PDE) inhibitor, a thyroid hormone agonist, a glucocorticoid receptor antagonist, a stearoyl-CoA-desaturase (SCD) inhibitor, a phosphate transport, glucose transport, fatty acid transport or dicarboxylate transport modulator, a $5HT_2$ antagonist, a $5HT_6$ antagonist or a bombesin agonist.

The term "opioid antagonist" is intended to mean a compound such as naltrexone, naloxone or nalmefen.

The expression "agent that can be used in the treatment of alcoholism and withdrawal symptoms" is intended to mean acamprosate, benzodiazepines, beta-blockers, clonidine or carbamazepine.

The expression "agent that can be used for treating osteoporosis" is intended to mean, for example, bisphosphonates such as etidronate, clodronate, tiludronate or risedronate.

According to the present invention, other compounds with antihyperlipemic, antihypercholesterolemic, antidiabetic or anti-obesity properties may also be combined. More particularly, compounds belonging to one of the following classes may be combined:

PTP 1 B (Protein Tyrosine Phosphase—1B) inhibitors, VPAC 2 receptor agonists, GLK modulators, retinoid modulators, glycogen phosphorylase (HGLPa) inhibitors, glucagon antagonists, glucose-6-phosphate inhibitors, pyruvate dehydrogenase kinase (PKD) activators, RXR, FXR or LXR modulators, SGLT (Sodium Dependent Glucose Transporter) inhibitors, CETP (Cholesteryl Ester Transfer Protein) inhibitors, squalene synthetase inhibitors, squalene epoxidase inhibitors, triglyceride synthesis inhibitors, LDL (Low Density Lipoprotein) receptor inducers, IBAT inhibitors, FBPase (fructose-1,6-biphosphatase) inhibitors, CART (Cocaine-Amphetamine-Regulated Transcript) modulators modulators and orexin receptor antagonists.

According to another aspect of the invention, the compound of Formula (I), or a pharmaceutically acceptable salt thereof, and the other active ingredient combined can be administered simultaneously, separately or sequentially over time.

The term "simultaneous use" is intended to mean the administration of the compounds of the composition according to the invention within one and the same pharmaceutical form.

The term "separate use" is intended to mean the administration, at the same time, of the two compounds of the composition according to the invention, each within a separate pharmaceutical form.

The term "sequential use over time" is intended to mean the successive administration of the first compound of the composition of the invention, within one pharmaceutical form, and then the second compound of the composition according to the invention, within a separate pharmaceutical form. In this case, the time elapsed between the administration of the first compound of the composition according to the invention and the administration of the second compound of the same composition according to the invention does not generally exceed 24 hours.

In the pharmaceutical compositions of the present invention for oral, sublingual, subcutaneous, intramuscular, intravenous, topical, local, intratracheal, intranasal, transdermal or rectal administration, the active ingredient of Formula (I) above, or the optional salt thereof, can be administered in a unit administration form, as a mixture with conventional pharmaceutical excipients, to animals and to human beings for the prophylaxis or treatment of the above disorders or diseases.

The appropriate unit administration forms include forms for oral administration, such as tablets, soft or hard gel capsules, powders, granules and oral solutions or suspensions, sublingual, buccal, intratracheal, intraocular and intranasal administration forms, forms for administration by inhalation, topical, transdermal, subcutaneous, intramuscular or intravenous administration forms, rectal administration forms, and implants. For topical application, the compounds according to the invention can be used in creams, gels, ointments or lotions.

By way of example, a unit administration form of a compound according to the invention in tablet form may comprise the following components:

| | |
|---|---:|
| Composition according to the invention | 50.0 mg |
| Mannitol | 223.75 mg |
| Sodium croscarmellose | 6.0 mg |
| Maize starch | 15.0 mg |
| Hydroxypropylmethylcellulose | 2.25 mg |
| Magnesium stearate | 3.0 mg |

By oral administration, the dose of active ingredient administered per day can reach 0.01 to 100 mg/kg, taken as one or more dosage intakes, preferably 0.02 to 50 mg/kg.

There may be specific cases where higher or lower dosages are appropriate: such dosages do not depart from the context of the invention. According to the usual practice, the dosage suitable for each patient is determined by the physician according to the method of administration and the weight and response of said patient.

According to another of its aspects, the present invention also relates to a method for treating the pathologies indicated above, which comprises the administration, to a patient, of an effective dose of a compound according to the invention, or a pharmaceutically acceptable salt thereof.

The invention claimed is:
1. A compound of Formula (I):

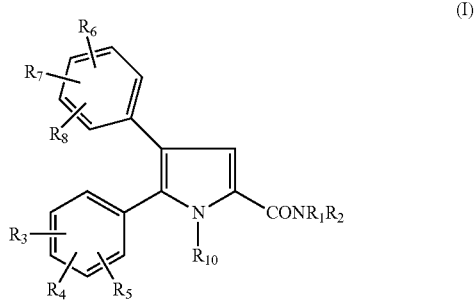

in which:
R$_1$ represents a hydrogen atom or a (C$_1$-C$_4$)alkyl group which is unsubstituted or substituted with one or more fluorine atoms;

R$_2$ represents:
either a homopiperidin-1-yl, piperidin-1-yl, pyrrolidin-1-yl or azetidin-1-yl radical, said radicals being unsubstituted or substituted once or twice with a substituent, each chosen independently from a fluorine atom, a (C$_1$-C$_4$)alkyl, (C$_1$-C$_4$)alkoxyl, trifluoromethyl, —OCF$_3$, CH$_2$OH, —CONH$_2$ or a phenyl group, said phenyl group being unsubstituted or substituted once or twice with a substituent, each chosen independently from a halogen atom, a —CF$_3$ group, a methoxyl group or a trifluoromethoxyl group;

or an amino(C$_1$-C$_6$)alkyl group which is unsubstituted or substituted with one or more substituents, each chosen independently from a fluorine atom, a hydroxyl group, a —CONH$_2$ group or a phenyl group, said phenyl group being unsubstituted or substituted once or twice with a substituent, each chosen independently from a halogen atom, a —CF$_3$ group, a methoxyl group or a trifluoromethoxyl group;

or R$_1$ and R$_2$, together with the nitrogen atom to which they are attached, constitute:
either a piperazin-1-yl or 1,4-diazepan-1-yl radical, said radicals being unsubstituted or substituted with a substituent chosen from a phenyl, benzodioxolyl, benzodioxolylmethyl, tetrahydrofuranylcarbonyl, —$COR_{11}$, or —$CH_2COR_{11}$ group, the phenyl group itself being unsubstituted or substituted one or more times with a substituent, each chosen independently from a halogen atom, or a ($C_1$-$C_4$)alkyl, trifluoromethyl, hydroxyl, ($C_1$-$C_4$)alkoxyl or cyano group;

or a homopiperidin-1-yl, piperidin-1-yl, pyrrolidin-1-yl or azetidin-1-yl radical, said radicals being unsubstituted or substituted once or twice with a substituent, each independently chosen from:

a fluorine atom, or a cyano, —$COR_{11}$, —$NR_{12}R_{13}$, —$NHCOR_{14}$, —$CH_2COR_{11}$, —$SO_2R_{14}$, or —$SO_2NR_{12}R_{13}$ group;

or a phenyl group or a pyridinyl group; said groups being unsubstituted or substituted one or more times with a substituent, each chosen independently from a halogen atom, or a ($C_1$-$C_4$)alkyl, trifluoromethyl, hydroxyl, ($C_1$-$C_4$)alkoxyl or cyano group;

or a benzyl group which is unsubstituted or substituted one or more times with a substituent, each chosen independently from a halogen atom, or a ($C_1$-$C_4$)alkyl, trifluoromethyl, hydroxyl, ($C_1$-$C_4$)alkoxyl or cyano group;

or a piperidin-1-yl, pyrrolidin-1-yl or azetidin-1-yl group, said groups being unsubstituted or substituted one or more times with a substituent, each chosen independently from a fluorine atom, or a ($C_1$-$C_4$)alkyl, ($C_1$-$C_4$)alkoxyl, hydroxyl, trifluoromethyl or $OCF_3$ group;

or an aminophenyl or aminobenzyl group, said groups being unsubstituted or substituted one or more times with a substituent, each chosen independently from a halogen atom, or a ($C_1$-$C_4$)alkyl, trifluoromethyl, hydroxyl, ($C_1$-$C_4$)alkoxyl or cyano group;

or an amino($C_1$-$C_6$)alkyl group which is unsubstituted or substituted one or more times with a substituent, each chosen independently from a halogen atom, a hydroxyl group, a ($C_1$-$C_4$)alkoxyl group or a cyano group;

or an amino($C_3$-$C_7$)cycloalkyl group which is unsubstituted or substituted one or more times with a substituent, each chosen independently from a halogen atom, a hydroxyl group, a ($C_1$-$C_4$)alkyl group, a ($C_1$-$C_4$)alkoxyl group or a cyano group, said ($C_1$-$C_4$)alkyl group being unsubstituted or substituted one or more times with a fluorine atom;

$R_3$, $R_4$, $R_5$, $R_6$, $R_7$, $R_8$ each independently represent a hydrogen atom, a halogen atom, a —CN, —$S(O)_nR_{14}$ or —$OSO_2R_{14}$ group, or a ($C_1$-$C_6$)alkyl group which is unsubstituted or substituted one or more times with a fluorine atom or a ($C_1$-$C_6$)alkoxyl group which is unsubstituted or substituted with one or more fluorine atoms, on the condition that one of the two substituents $R_3$ and $R_6$ represents a Y-A-$R_9$ group;

Y represents an oxygen atom;

A represents a ($C_1$-$C_4$) alkylene group which is unsubstituted or substituted one or more times with a substituent, each chosen independently from a ($C_1$-$C_3$) alkyl group or with a fluorine atom;

$R_9$ represents an —$OR_{12}$, —CN, —$CO_2H$, $NR_{12}R_{13}$, —$CONR_{12}R_{13}$, —$NR_{15}COR_{12}$, —$CONHNH_2$, —CONHOH, —$CONHSO_2R_{14}$, —$S(O)_9R_{14}$, —$SO_2NR_{12}R_{13}$, —$NR_{18}SO_2R_{14}$ or —$NR_{15}SO_2NR_{12}R_{13}$;

$R_{10}$ represents a hydrogen or a ($C_1$-$C_4$)alkyl group;

$R_{11}$ represents:

a ($C_1$-$C_4$)alkyl, phenyl, benzyl, ($C_1$-$C_4$)alkoxyl or ($C_1$-$C_3$)alkylene-O—($C_1$-$C_3$)alkyl group, said groups being unsubstituted or substituted with one or more substituents, each chosen independently from a ($C_1$-$C_4$)alkoxyl group, a hydroxyl group or a fluorine atom;

a trifluoromethyl;

or an —$NR_{16}R_{17}$ group;

$R_{12}$ and $R_{13}$ each independently represent a hydrogen atom or a ($C_1$-$C_6$)alkyl group optionally substituted with one or more substituents, each chosen independently from a fluorine atom, —OH or —$OR_{14}$, or $R_{12}$ and $R_{13}$, together with the nitrogen atom to which they are attached, constitute a 4- to 7-membered heterocyclic radical which may comprise a second heteroatom chosen from a nitrogen, oxygen or sulphur atom;

n represents 0, 1 or 2;

$R_{14}$ represents a ($C_1$-$C_4$)alkyl group which is unsubstituted or substituted with one or more fluorine atoms;

$R_{15}$ represents a hydrogen atom or a ($C_1$-$C_4$)alkyl group;

$R_{16}$ and $R_{17}$ each independently represent:

a hydrogen atom;

or a benzyl group which is unsubstituted or substituted one or more times with a substituent, each chosen independently from a halogen atom, or a ($C_1$-$C_4$)alkyl, trifluoromethyl, hydroxyl, ($C_1$-$C_4$)alkoxyl or cyano group;

or a ($C_1$-$C_6$)alkyl group optionally substituted with one or more substituents, each chosen independently from a halogen atom, —OH or —$OR_{14}$;

$R_{18}$ represents a hydrogen atom or a ($C_1$-$C_4$)alkyl group which is unsubstituted or substituted with one or more fluorine atoms;

Alk represents a ($C_1$-$C_4$)alkyl group;

or the salt thereof.

2. The compound according claim 1, characterized in that the substituent $R_6$ represents a Y-A-$R_9$ group and the substituent $R_3$ represents a hydrogen atom, a halogen atom, a —CN, —$S(O)_6R_{14}$ or —$OSO_2R_{14}$ group, a ($C_1$-$C_6$)alkyl group which is unsubstituted or substituted one or more times with a fluorine atom, or a ($C_1$-$C_6$)alkoxyl group which is unsubstituted or substituted with one or more fluorine atoms, or the salt thereof.

3. The compound according to claim 1, characterized in that the substituent $R_3$ represents a Y-A-$R_9$ group and a substituent $R_6$ represents a hydrogen atom, a halogen atom, a —CN, —$S(O)_nR_{14}$ or —$OSO_2R_{14}$ group, a ($C_1$-$C_6$)alkyl group which is unsubstituted or substituted one or more times with a fluorine atom, or a ($C_1$-$C_6$)alkoxyl group which is unsubstituted or substituted with one or more fluorine atoms, or the salt thereof.

4. The compound according to claim 1, characterized in that A represents an unsubstituted ($C_1$-$C_4$) alkylene group, or the salt thereof.

5. The compound according to claim 1, characterized in that:

$R_1$ represents a hydrogen atom or a ($C_1$-$C_4$)alkyl group which is unsubstituted or substituted with one or more fluorine atoms;

$R_2$ represents:

either a homopiperidin-1-yl, piperidin-1-yl, pyrrolidin-1-yl or azetidin-1-yl radical, said radicals being substituted once or twice with a substituent, each chosen independently from a fluorine atom, a ($C_1$-$C_4$)alkyl, ($C_1$-$C_4$) alkoxyl, trifluoromethyl, —$OCF_3$, —$CH_2OH$ or —$CONH_2$ group or a phenyl group, said phenyl group being unsubstituted or substituted once or twice with a substituent, each chosen independently from a halogen atom, a —$CF_3$ group, a methoxyl group or a trifluoromethoxyl group;

or an amino($C_1$-$C_6$)alkyl group substituted with one or more substituents, each chosen independently from a fluorine atom, a hydroxyl group, a —$CONH_2$ group or a phenyl group, said phenyl group being unsubstituted or substituted once or twice with a substituent, each independently chosen from a halogen atom, a —$CF_3$ group, a methoxyl group or a trifluoromethoxyl group;

and the salt thereof.

6. The compound according to claim 5, characterized in that $R_2$ radical represents in particular a homopiperidin-1-yl, piperidin-1-yl, pyrrolidin-1-yl or azetidin-1-yl radical, said radicals being substituted once or twice with a substituent, each chosen independently from a fluorine atom, a ($C_1$-$C_4$) alkyl, ($C_1$-$C_4$)alkoxyl, trifluoromethyl, —$OCF_3$, —$CH_2OH$ or —$CONH_2$ group or a phenyl group, said phenyl group being unsubstituted or substituted once or twice with a substituent, each chosen independently from a halogen atom, a —$CF_3$ group, a methoxyl group or a trifluoromethoxyl group;

or the salt thereof.

7. The compound according to claim 1, characterized in that:

$R_1$ and $R_2$, together with the nitrogen atom to which they are linked, constitute:

either a piperazin-1-yl or 1,4-diazepan-1-yl radical, said radicals being substituted with a substituent chosen from a phenyl, benzodioxolyl, benzodioxolylmethyl, tetrahydrofuranylcarbonyl, —$COR_{11}$ or —$CH_2COR_{11}$ group, the phenyl group itself being unsubstituted or substituted one or more times with a substituent, each chosen independently from a halogen atom, a ($C_1$-$C_4$)alkyl group, a trifluoromethyl group, a hydroxyl group, a ($C_1$-$C_4$)alkoxyl group or a cyano group;

or a homopiperidin-1-yl, piperidin-1-yl, pyrrolidin-1-yl or azetidin-1-yl radical, said radicals being substituted once or twice with a substituent, each chosen independently from:

a fluorine atom, or a cyano, —$COR_{11}$, —$NR_{12}R_{13}$, —NH-$COR_{14}$, —$CH_2COR_{11}$, —$SO_2NR_{14}$ or —$SO_2NR_{12}R_{13}$ group;

or a phenyl or pyridinyl group; said groups being unsubstituted or substituted one or more times with a substituent, each chosen independently from a halogen atom, a ($C_1$-$C_4$)alkyl group, a trifluoromethyl group, a hydroxyl group, a ($C_1$-$C_4$)alkoxyl group or a cyano group;

or a benzyl group substituted one or more times with a substituent, each chosen independently from a halogen atom, a ($C_1$-$C_4$)alkyl group, a trifluoromethyl group, a hydroxyl group, a ($C_1$-$C_4$)alkoxyl group or a cyano group;

or a piperidin-1-yl, pyrrolidin-1-yl or azetidin-1-yl group, said groups being unsubstituted or substituted one or more times with a substituent, each chosen independently from a fluorine atom, a ($C_1$-$C_4$)alkyl group, a ($C_1$-$C_4$)alkoxyl group, a hydroxyl group, a trifluoromethyl group or an $OCF_3$ group;

or an aminophenyl or aminobenzyl group, said groups being unsubstituted or substituted one or more times with a substituent, each chosen independently from a halogen atom, a ($C_1$-$C_4$)alkyl group, a trifluoromethyl group, a hydroxyl group, a ($C_1$-$C_4$)alkoxyl group or a cyano group;

or an amino ($C_1$-$C_6$)alkyl group which is unsubstituted or substituted one or more times with a substituent, each chosen independently from a halogen atom, a hydroxyl group, a ($C_1$-$C_4$)alkoxyl group or a cyano group;

or an amino ($C_3$-$C_7$)cycloalkyl group which is unsubstituted or substituted one or more times with a substituent, each chosen independently from a halogen atom, a hydroxyl group, a ($C_1$-$C_4$)alkyl group, a ($C_1$-$C_4$)alkoxyl group or a cyano group, said ($C_1$-$C_4$)alkyl group being unsubstituted or substituted one or more times with a fluorine atom;

or the salt thereof.

8. The compound according to claim 7, characterized in that:

$R_1$ and $R_2$, together with the nitrogen atom to which they are attached, constitute a homopiperidin-1-yl, piperidin-1-yl, pyrrolidin-1-yl or azetidin-1-yl radical, said radicals being substituted once or twice with a substituent, each chosen independently from:

a fluorine atom, or a cyano, —$COR_{11}$, —$NR_{12}R_{13}$, —NH-$COR_{14}$, —$CH_2COR_{11}$, —$SO_2R_{14}$ or —$SO_2NR_{12}R_{13}$ group;

or a phenyl or pyridinyl group; said groups being unsubstituted or substituted one or more times with a substituent, each chosen independently from a halogen atom, a ($C_1$-$C_4$)alkyl group, a trifluoromethyl group, a hydroxyl group, a ($C_1$-$C_4$)alkoxyl group or a cyano group;

or a benzyl group substituted one or more times with a substituent, each chosen independently from a halogen atom, a ($C_1$-$C_4$)alkyl group, a trifluoromethyl group, a hydroxyl group, a ($C_1$-$C_4$)alkoxyl group and a cyano group;

or a piperidin-1-yl, pyrrolidin-1-yl or azetidin-1-yl group, said groups being unsubstituted or substituted one or more times with a substituent, each chosen independently from a fluorine atom, a ($C_1$-$C_4$)alkyl group, a ($C_1$-$C_4$)alkoxyl group, a hydroxyl group, a trifluoromethyl group or an —$OCF_3$ group;

or an aminophenyl or aminobenzyl group, said groups being unsubstituted or substituted one or more times with a substituent, each chosen independently from a halogen atom, a ($C_1$-$C_4$)alkyl group, a trifluoromethyl group, a hydroxyl group, a ($C_1$-$C_4$)alkoxyl group or a cyano group;

or an amino($C_1$-$C_6$)alkyl group which is unsubstituted or substituted one or more times with a substituent, each chosen independently from a halogen atom, a hydroxyl group, a ($C_1$-$C_4$)alkoxyl group or a cyano group;

or an amino ($C_3$-$C_7$)cycloalkyl group which is unsubstituted or substituted one or more times with a substituent, each chosen independently from a halogen atom, a hydroxyl group, a ($C_1$-$C_4$)alkyl group, a ($C_1$-$C_4$)alkoxyl group or a cyano group, said ($C_1$-$C_4$)alkyl group being unsubstituted or substituted one or more times with a fluorine atom;

or the salt thereof.

9. The compound according to claim 1, characterized in that the compound is chosen from the group consisting of:

1-[4-(2,4-dichlorophenyl)-5-[4-(4-hydroxypropoxy)phenyl]-1-methyl-1H-pyrrole-2-carbonyl]-4-(3-fluorobenzylamino)piperidine-4-carboxamide, 1-[5-(4-carbamoylmethoxy)phenyl-4-(2,4-dichlorophenyl)-1-methyl-1H-pyrrole-2-carbonyl]-4-phenylpiperidine-4-carboxamide, and 1-[4-(2-chlorophenyl)-5-[4-(4-hydroxypropoxy)phenyl]-1-methyl-1H-pyrrole-2-carbonyl]-4-(4-fluoro-benzylamino)piperidine-4-carboxamide, or the salts thereof.

10. A pharmaceutical composition, characterized in that it comprises a compound of Formula (I) according to claim 1, or the pharmaceutically acceptable salt thereof and at least one pharmaceutically acceptable excipient.

* * * * *